US008501722B2

(12) United States Patent
Ginsburg et al.

(10) Patent No.: US 8,501,722 B2
(45) Date of Patent: Aug. 6, 2013

(54) METHODS AND COMPOSITIONS FOR TREATING BACTERIAL INFECTION

(75) Inventors: David Ginsburg, Ann Arbor, MI (US); Hongmin Sun, Columbia, MO (US); Scott Larsen, South Lyon, MI (US); Bryan Yestrepsky, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 446 days.

(21) Appl. No.: 12/691,286

(22) Filed: Jan. 21, 2010

(65) Prior Publication Data

US 2010/0331351 A1 Dec. 30, 2010

Related U.S. Application Data

(60) Provisional application No. 61/146,143, filed on Jan. 21, 2009.

(51) Int. Cl.
*A01N 43/00* (2006.01)
*A61K 31/33* (2006.01)

(52) U.S. Cl.
USPC .............. 514/183; 514/267; 514/257; 506/2; 544/230; 544/249

(58) Field of Classification Search
USPC ...................... 514/267, 257; 506/2; 544/230, 544/249
See application file for complete search history.

(56) References Cited

U.S. PATENT DOCUMENTS 3,257,400 A 6/1966 Wagner

FOREIGN PATENT DOCUMENTS

WO 2007037193 A1 2/2007
WO 2007082178 A2 7/2007

OTHER PUBLICATIONS

STN Accession No. 2009:846107 CAPLUS as evidenced by WU 2009/0163545, published on Jun. 25, 2009 and filed on Dec. 21, 2007.*
Markyosan et al, Pharmaceutical Chemistry Journal, vol. 40, No. 9, 2006.*
Bax et al., "The millennium bugs—the need for and development of new antibacterials." Int. J. Antimicrob. Agents 2000, 16:51-59.
Norrby et al., "Lack of development of new antimicrobial drugs: a potential serious threat to public health." Lancet Infect. Dis. 2005, 5:115-119.
Silver, "Multi-targeting by monotherapeutic antibacterials." Nat. Rev. Drug Discov. 2007, 6:41-55.
Steiner et al., "Dual control of streptokinase and streptolysin S production by the covRS and fasCAX two-component regulators in *Streptococcus dysgalactiae* subsp. *equisimilis*."Infect. Immun. 2002, 70:3627-3636.
Hashikawa et al., "Characterization of group C and G streptococcal strains that cause streptococcal toxic shock syndrome." J.Clin. Microbiol. 2004, 42:186-192.
Pinho et al., "Clonal Relationships between Invasive and Noninvasive Lancefield Group C and G Streptococci and emm-Specific Differences in Invasiveness" J. Clin. Microbiol. 2006, 44:841-846.
Sylvetsky et al., "Bacteremia due to beta-hemolytic *Streptococcus* group G: increasing incidence and clinical characteristics of patients." Am. J. Med. 2002, 112:622-626.
Harrington et al., "The molecular basis of *Streptococcus equi* infection and disease." Microbes. Infect. 2002, 4:501-510.
Bradley, "Bovine mastitis: an evolving disease." Vet. J. 2002;164:116-128.
Leigh, "*Streptococcus uberis*: a permanent barrier to the control of bovine mastitis?" Vet. J. 1999, 157(3):225-238.
Marcum et al., "Species specificity of streptokinase." Comp Biochem. Physiol B 1983, 75(3):389-394.
Bugge et al., "Plasminogen deficiency causes severe thrombosis but is compatible with development and reproduction." Genes Dev. 1995, 9:794-807.
Ploplis et al., "Effects of disruption of the plasminogen gene on thrombosis, growth, and health in mice." Circulation 1995, 92:2585-2593.
Mann et al., "Factor V: a combination of Dr Jekyll and Mr Hyde." Blood 2003, 101:20-30.
Kisiel et al., "Anticoagulant properties of bovine plasma protein C following activation by thrombin." Biochemistry 1977, 16:5824-5831.
Rosing et al., "Coagulation factor V: an old star shines again." Thromb. Haemost. 1997, 78(1):427-433.
Guinto et al., "Loss of prothrombin and of factor Xa-factor Va interactions upon inactivation of factor Va by activated protein C." J. Biol. Chem. 1984, 259:13986-13992.
Boyle et al., "The interaction of pathogens with humans." Methods 2000, 21:99-102.
Suh et al., "Resolution of spontaneous bleeding events but failure of pregnancy in fibrinogen-deficient mice." Genes Dev. 1995, 9:2020-2033.
Flick et al., "Fibrin(ogen)-alpha M beta 2 interactions regulate leukocyte function and innate immunity in vivo." Exp. Biol. Med. (Maywood.) 2004, 229:1105-1110.
Flick et al., "Leukocyte engagement of fibrin(ogen) via the integrin receptor alphaMbeta2/Mac-1 is critical for host inflammatory response in vivo." J. Clin. Invest 2004, 113:1596-1606.
Khil et al., "Plasminogen enhances virulence of group A streptococci by streptokinase-dependent and streptokinase-independent mechanisms." J. Infect. Dis. 2003, 188:497-505.
Ringdahl et al., "Molecular co-operation between protein PAM and streptokinase for plasmin acquisition by *Streptococcus pyogenes*." J. Biol. Chem. 1998, 273:6424-6430.
Heath et al., "A two-component regulatory system, CsrR-CsrS, represses expression of three *Streptococcus pyogenes* virulence factors, hyaluronic acid capsule, streptolysin S, and pyrogenic exotoxin B." Infect. Immun. 1999, 67:5298-5305.
Rezcallah et al., "Mouse skin of *Streptococcus pyogenes* results in increase streptokinase expression and activity." Microbiology 2004, 150:365-371.

(Continued)

*Primary Examiner* — Brandon Fetterolf
*Assistant Examiner* — Jean Cornet
(74) *Attorney, Agent, or Firm* — Casimir Jones, S.C.

(57) ABSTRACT

The present invention relates to chemical compounds, methods for their discovery, and their therapeutic and research use. In particular, the present invention provides compounds as therapeutic agents against bacterial infections.

7 Claims, 19 Drawing Sheets

OTHER PUBLICATIONS

Bhatia et al., "Solution Phase Comnibactorial Synthesis and Screening of Mini Libraries of Arylchalcones for Antibacterial Activity." Sci. Pharm 2008, 76:259-267.
Bisno et al., "Streptococcal infections of skin and soft tissues." N. Engl. J. Med. 1996, 334(4):240-245.
Carapetis et al., "The global burden of group A streptococcal diseases." Lancet Infect. Dis. 2005, 5:685-694.
Efstratiou et al., "Group A streptococci in the 1990s." J. Antimicrob. Chemother. 2000, 45 Suppl:3-12.
Stevens, "Invasive group A *Streptococcus* infections."Clin. Infect. Dis. 1992, 14:2-11.
Broeseker et al., "Characterization of the Interaction of human plasmin with its specific receptor on a group A *Streptococcus*." Microb. Pathog. 1988, 5:19-27.
D'Costa et al., "Interaction of group A *Streptococci* with human plasmin(ogen) under physiological conditions." Methods 2000, 21:165-177.
DesJardin et al., "Group A streptococci bind human plasmin but not other structurally related proteins." Thromb. Res. 1989, 55(2):187-193.
Li et al., "Interaction between group A streptococci and the plasmin(ogen) system promotes virulence in a mouse skin infection model." J. Infect. Dis. 1999, 179:907-914.
Christner et al., "Identification of key gene products required for acquisition of plasmin-like enzymatic activity by group A streptococci." J. Infect. Dis. 1997, 175 (5):1115-1120.
Lottenberg et al., "Identification of a specific receptor for plasmin on a group A *Streptococcus*." Infect. Immun. 1987, 55 (8):1914-1918.
Lottenberg et al., "Streptokinase-producing streptococci grown in human plasma acquire unregulated cell-associated plasmin activity." J. Infect. Dis. 1992, 166(2):436-440.
Wang et al., "A role for fibrinogen in the streptokinase-dependent acquisition of plasmin(ogen) by group A streptococci." J. Infect. Dis. 1995, 171(1):85-92.
Wang et al., "Analysis of the interaction of group A streptococci with fibrinogen, streptokinase and plasminogen." Microb. Pathog. 1995, 18:153-166.
Coleman et al., "*Borrelia burgdorferi* binds plasminogen, resulting in enhanced penetration of endothelial monolayers." Infect. Immun. 1995, 63:2478-2484.
Coleman et al., "Plasminogen is required for efficient dissemination of *B. burgdorferi* in ticks and for enhancement of spirochetemia in mice." Cell 1997, 89:1111-1119.
Sodeinde et al., "A surface protease and the invasive character of plague." Science 1992;258:1004-1007.
McDonough et al., "A *Yersinia* pestis-specific DNA fragment encodes temperature-dependent coagulase and fibrinolysin-associated phenotypes." Mol. Microbiol. 1989, 39(6):767-775.
McDonough et al., "Mutation in the pla gene of *Yersinia pestis* alters the course of the plague *Bacillus*-flea (Siphonaptera: Ceratophyllidae) interaction." J. Med. Entomol. 1993, 30:772-780.
Sodeinde et al., "Genetic analysis of the 9.5-kilobase virulence plasmid of *Yersinia pestis*." Infect. Immun. 1988, 56:2743-2748.
Boyle et al., Thromb. Haemost. "Plasminogen activation by invasive human pathogens." 1997, 77(1):1-10.
Coleman et al., "Use of the plasminogen activation system by microorganisms." J. Lab Clin. Med. 1999, 134(6):567-576.
Lahteenmaki et al., "Bacterial plasminogen activators and receptors." FEMS Microbiol. Rev. 2001, 25(5):531-552.
Tillett et al., "The Fibrinolytic Activity of Hemolytic Streptococci." J. Exp. Med. 1933, 58:485-502.
Marcum et al., "Species specificity of streptokinase." Comp Biochem. Physiol B 1983, 75:389-394.
Nowicki et al., "Characterization of a novel streptokinase produced by *Streptococcus equisimilis* of non-human origin." Thromb. Haemost. 1994, 72:595-603.

McCoy et al., "Streptokinases produced by pathogenic group C streptococci demonstrate species-specific plasminogen activation." J. Infect. Dis. 1991, 164:515-521.
Schroeder et al., "Species specificity of plasminogen activation and acquisition of surface-associated proteolytic activity by group C streptococci grown in plasma." Infect. Immun. 1999, 67(12):6487-6495.
Lijnen et al., "Fibrinolytic agents: mechanisms of activity and pharmacology." Thromb. Haemost. 1995, 74:387-390.
Metz et al., "Randomized comparison of direct thrombin inhibition versus heparin in conjunction with fibrinolytic therapy for acute myocardial infarction: results from the GUSTO-IIb Trial. Global Use of Strategies to Open Occluded Coronary Arteries in Acute Coronary Syndromes (GUSTO-IIb) Investigators." J. Am. Coll. Cardiol. 1998, 31:1493-1498.
Esmon et al., "Switching serine protease specificity." Nat. Struct. Biol. 1998, 5(11):933-937.
Reed et al., "A catalytic switch and the conversion of streptokinase to a fibrin-targeted plasminogen activator." 10 Proc. Natl. Acad. Sci. U.S.A 1999, 969(16):8879-8883.
Sun et al., "Plasminogen is a critical host pathogenicity factor for group A streptococcal infection." Science 2004, 305:1283-1286.
Esmon, "The impact of the inflammatory response on coagulation." Thromb. Res. 2004, 114:321-327.
Levi et al., "Endothelium: interface between coagulation and inflammation." Crit Care Med. 2002, 30:S220-S224.
Levi et al., "Infection and inflammation and the coagulation system." Cardiovasc. Res. 2003, 60(1):26-39.
Levi et al., "Bidirectional relation between inflammation and coagulation." Circulation 2004, 109:2698-2704.
Mundada et al., "Structure-function analysis of the streptokinase amino terminus (residues 1-59)." J. Biol. Chem. 2003, 278:24421-24427.
Sun, "The interaction between pathogens and the host coagulation system." Physiology (Bethesda.) 2006, 21:281-288.
Ferretti et al., "Complete genome sequence of an M1 strain of *Streptococcus pyogenes*." Proc. Natl. Acad. Sci. U.S.A 2001, 98:4658-4663.
Holden et al., "Complete genome of acute rheumatic fever-associated serotype M5 *Streptococcus pyogenes* strain manfredo." J. Bacteriol. 2007, 189:1473-1477.
Nakagawa et al., "Genome sequence of an M3 strain of *Streptococcus pyogenes* reveals a large-scale genomic rearrangement in invasive strains and new insights into phage evolution." Genome Res. 2003, 13:1042-1055.
Kreikemeyer et al., "Virulence factor regulation and regulatory networks in *Streptococcus pyogenes* and their impact on pathogen-host interactions." Trends Microbiol. 2003, 11:224-232.
Graham et al., "Virulence control in group A *Streptococcus* by a two-component gene regulatory system: global expression profiling and in vivo infection modeling." Proc. Natl. Acad. Sci. U.S.A 2002, 99:13855-13860.
Malke et al., Control of streptokinase gene expression in group A & C streptococci by two-component regulators. Indian J. Med. Res. 2004, 119 Suppl:48-56.
Federle et al., "A response regulator that represses transcription of several virulence operons in the group A *Streptococcus*."J. Bacterial. 1999, 181:3649-3657.
Kreikemeyer et al., "Group A streptococcal growth phase-associated virulence factor regulation by a novel operon (Fas) with homologies to two-component-type regulators requires a small RNA molecule." Mol. Microbiol. 2001, 39:392-406.
Martinez et al., "Interactions among strategies associated with bacterial infection: pathogenicity, epidemicity, and antibiotic resistance." Clin. Microbial. Rev. 2002, 15:647-679.
Alanis, "Resistance to antibiotics: are we in the post-antibiotic era?" Arch. Med. Res. 2005, 36:697-705.

* cited by examiner

METHODS AND COMPOSITIONS FOR TREATING BACTERIAL INFECTION

CROSS REFERENCE TO RELATED APPLICATIONS

This application claims priority to provisional application Ser. No. 61/146,143, filed Jan. 21, 2009, which is herein incorporated by reference in its entirety.

STATEMENT REGARDING FEDERALLY SPONSORED RESEARCH OR DEVELOPMENT

This invention was made with government support under grant number PO1 HL 057346 awarded by the National Institutes of Health. The government has certain rights in the invention.

FIELD OF THE INVENTION

The present invention relates to chemical compounds, methods for their discovery, and their therapeutic and research use. In particular, the present invention provides compounds as therapeutic agents against bacterial infections.

BACKGROUND OF THE INVENTION

The prevalence of antibiotic resistances in bacteria is becoming one of the leading public health threats. Current antibiotics interfere with the critical biological processes of the pathogens and cause death or growth arrest of the bacteria. As a result, antibiotic therapy exerts a strong selective pressure to favor emergence of antibiotic resistant strains. In order to circumvent this serious problem, alternative antimicrobial reagents are needed that suppress the virulence of the pathogens without generating strong selection for antibiotic resistance.

Group A *streptococcus* is among the most common human pathogens. Group A streptococci (GAS), also known as *Streptococcus pyogenes*, causes a variety of pathologies in different systems. From 5-15% of normal individuals are estimated to harbor this bacterium without sign of disease. GAS is highly specific to its human host and rarely infects other species. Infections caused by GAS include both mild conditions, such as tonsillitis, scarlet fever and impetigo, as well as life threatening diseases, such as toxic-shock-like syndrome and necrotizing fasciitis (Bisno et al., N. Engl. J. Med. 1996; 334:240-245). Strep throat accounts for 5-10% of sore throat cases. Ten million cases of mild GAS infection, such as strep throat and impetigo, occur in the United States every year. If left untreated, strep throat can lead to rheumatic fever and rheumatic heart disease, causing at least 15.6 million cases and 282,000 new cases respectively and resulting in 233,000 deaths each year Worldwide (Carapetis et al., Lancet Infect. Dis. 2005; 5:685-694). Even though treatment with antibiotics has greatly reduced mortality in the developed world, according to American Heart Association statistics, rheumatic fever and rheumatic heart disease still accounted for 3,248 deaths in the US in 2004. Furthermore, emergence of epidemic invasive GAS diseases poses another critical medical challenge given that little is known about the mechanism of invasiveness (Bisno et al., supra; Efstratiou et al., J. Antimicrob. Chemother. 2000; 45 Suppl:3-12; Stevens, Clin. Infect. Dis. 1992; 14:2-11).

Additional therapies for GAS infection, an important public health problem given the alarming emergence of antibiotic resistance among nearly all major human pathogens, are needed.

SUMMARY

The present invention relates to chemical compounds, methods for their discovery, and their therapeutic and research use. In particular, the present invention provides compounds as therapeutic agents against bacterial infections.

In some embodiments, the present invention provides a composition that inhibits the pathogenticity of bacteria (e.g., Group A *Streptococcus*), comprising a compound that inhibits the expression or activity of streptokinase from the bacteria. In some embodiments, the compound has the structure

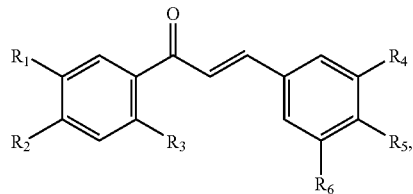

wherein R1 and R2 are selected from H, alkyl or O-alkyl, $R_3$ is an O-alkyl, $R_3$ is H or O-alkyl and, $R_4$, $R_5$ and $R_6$ are an O-alkyl. In some embodiments, the compound has the structure

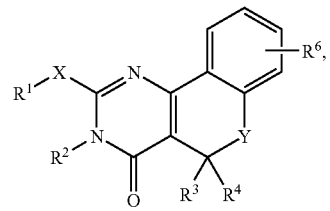

wherein $R^1$ is a C1-C6 alkyl, optionally substituted with CN, $OR^7$, $NR^7_2$, $CO_2R^7$, $CONHR^7$, heteroaryl, Ph, $R^2$ is a C1-C6 alkyl or alkenyl $R^3$ and $R^4$ are, independently, H, a C1-C6 alkyl or joined in a cycloalkyl ring of 3-7 carbons, and $R^6$ is H or one or more standard aryl substituents, $Y=(CH_2)_n$ or $CH-R^8$, n=0 or 1, $R^8=C1$-C6 alkyl.

In some embodiments, the compound is

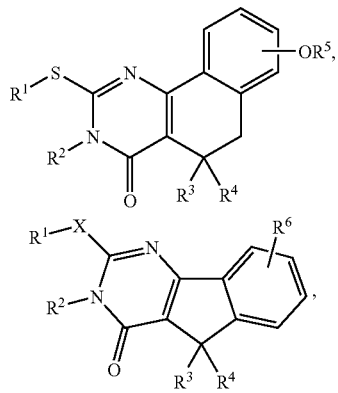

-continued

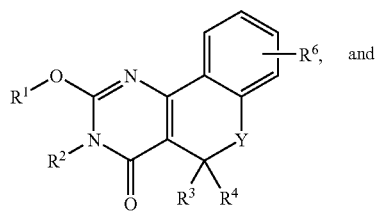

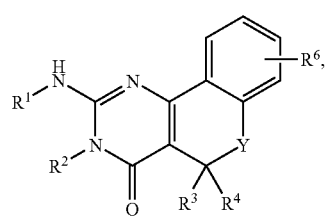

wherein X is S, O or NH, Y is $(CH_2)_n$ or $CH-R^8$, $R^1$ is a C1-C6 alkyl, optionally substituted with CN, $OR^7$, $NR^7{}_2$, $CO_2R^7$, $CONHR^7$, heteroaryl, Ph, $R^2$ is a C1-C6 alkyl or alkenyl $R^3$ and $R^4$ are, independently, H, a C1-C6 alkyl or joined in a cycloalkyl ring of 3-7 carbons $R^5$ is. C1-C6 alkyl, optionally substituted with CN, $OR^7$, $NR^7{}_2$, $CO_2R^7$, $CONHR^7$, heteroaryl, Ph, $SO_2R^7$, $NHCOR^7$, $SO_2NHR^7$, $OCOR^7$, $R^6$ is H or one or more standard aryl substituents and $R^7$=H or a C1-C3 alkyl, $R^8$ is a $C_1$-$C_6$ alkyl and n=0 or 1.

In other embodiments, the compound is, e.g.,

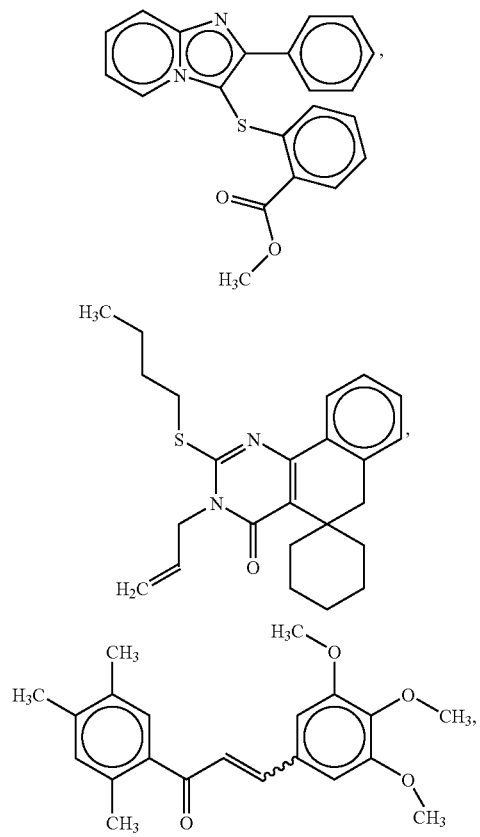

-continued

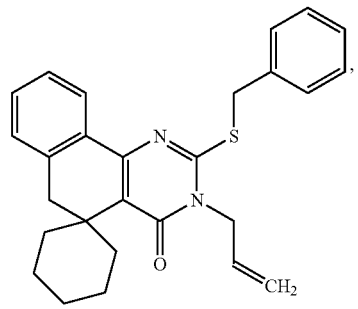

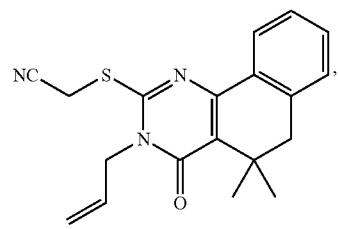

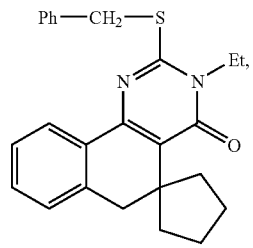

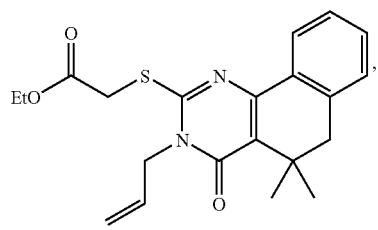

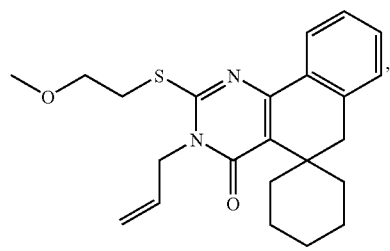

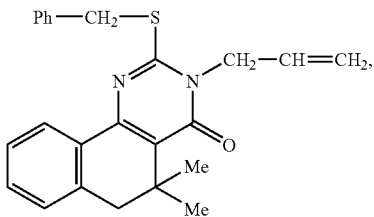

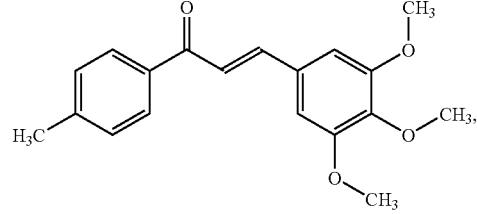

-continued
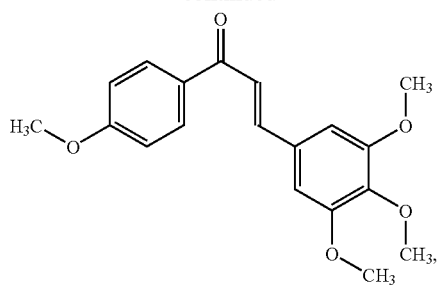
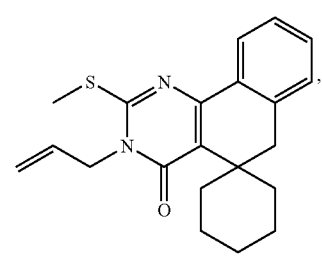
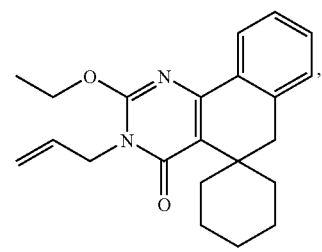
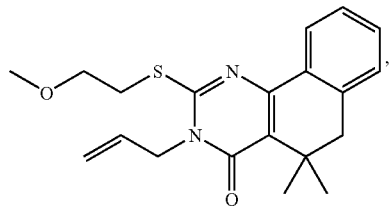
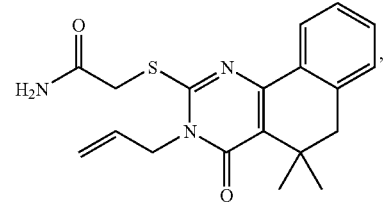
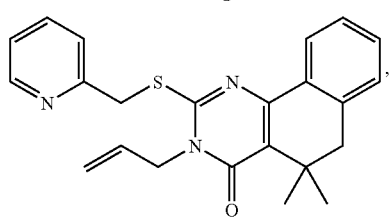
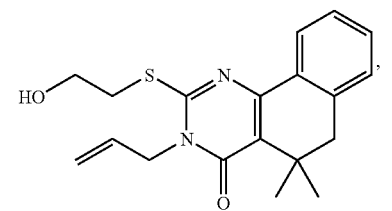
-continued
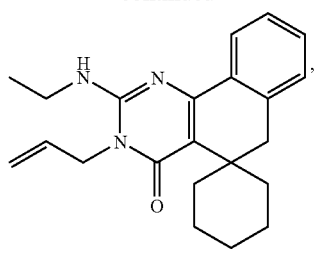
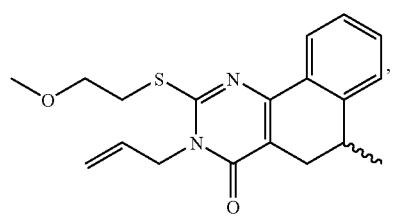
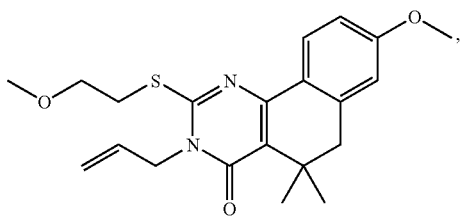
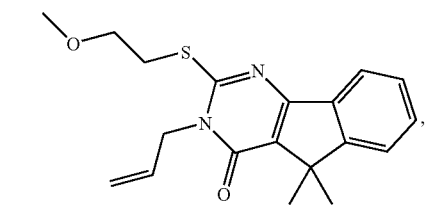
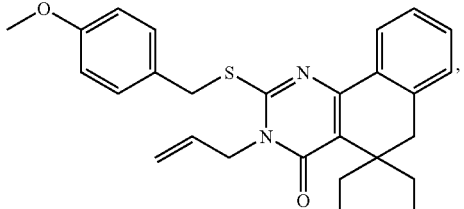
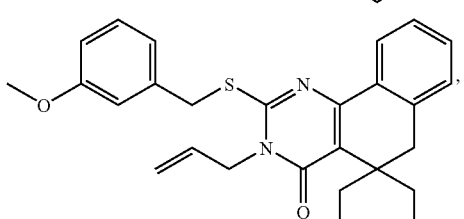
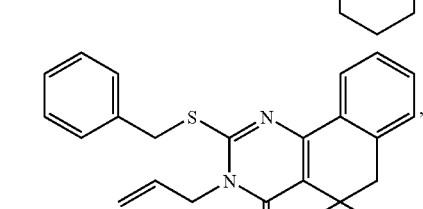

-continued

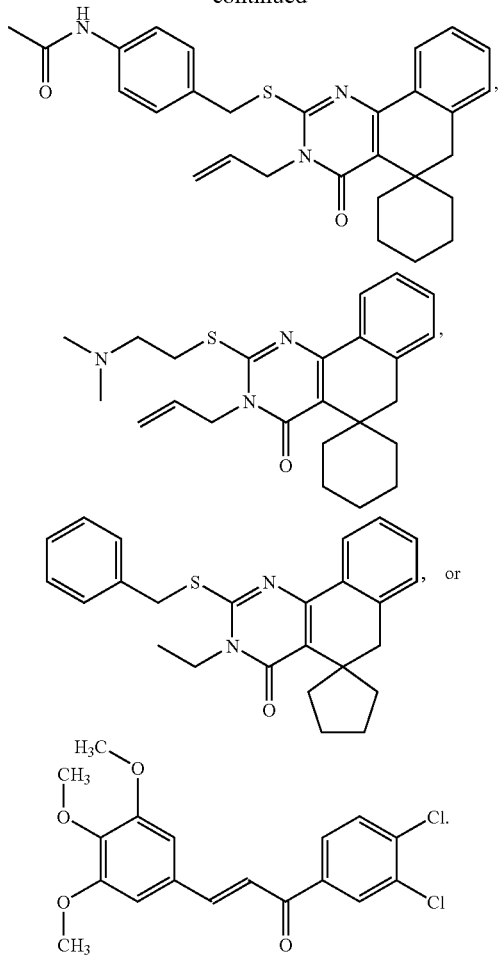

In some embodiments, the compound is an enantiomer, racemic mixture, derivative, or mimetic of the above described compounds. In some embodiments, the composition further comprises a pharmaceutically acceptable carrier. In some embodiments, the composition further comprises an antibiotic compound (e.g., a known antibiotic compound).

Other embodiments of the present invention provide a method of inhibiting the pathogenticity of a bacteria (e.g., Group A *Streptococcus*), comprising administering to a submit of sample (e.g., suspected of containing bacteria or known to contain bacteria) with a compound that inhibits the expression or activity of streptokinase from the bacteria (e.g., the compounds described above). In some embodiments, the method further comprises the step of contacting the bacteria with an antibiotic compound (e.g., a known antibiotic compound).

Further embodiments of the present invention provide a method (e.g., a high throughput method) of screening for compounds that inhibit the pathogenicity of a bacteria comprising a streptokinase gene (e.g., Group A *Streptococcus*), comprising: contacting samples comprising bacteria, wherein the bacteria comprises a selectable marker gene under the control of a streptokinase promoter, with a plurality of test compounds; and measuring the pathogenicity of the samples under selectable conditions. In some embodiments, the method further comprises the step of identifying test compounds that inhibit the pathogenicity of the bacterial samples.

DEFINITIONS

Figure 1:
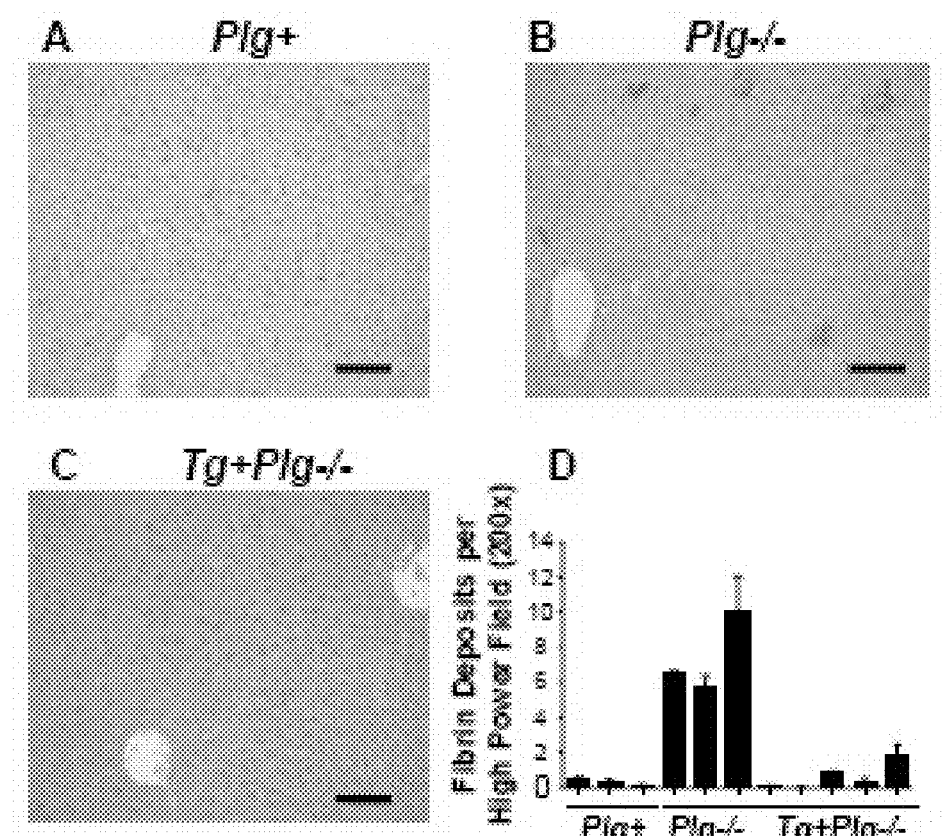
FIG. 1 shows human plasminogen transgene rescues mouse Plg−/− phenotype.

To facilitate an understanding of the present invention, a number of terms and phrases are defined below.

As used herein, the term "aliphatic" represents the groups including, but not limited to, alkyl, alkenyl, alkynyl, alicyclic.

As used herein, the term "alkyl" refers to an unsaturated carbon chain substituent group. In general, alkyls have the general formula $C_nH_{2+1}$. Exemplary alkyls include, but are not limited to, methyl ($CH_3$), ethyl ($C_2H_5$), propyl ($C_3H_7$), butyl ($C_4H_9$), pentyl ($C_5H_{11}$), etc.

As used herein, the term "aryl" represents a single aromatic ring such as a phenyl ring, or two or more aromatic rings (e.g., bisphenyl, naphthalene, anthracene), or an aromatic ring and one or more non-aromatic rings. The aryl group can be optionally substituted with a lower aliphatic group (e.g., alkyl, alkenyl, alkynyl, or alicyclic). Additionally, the aliphatic and aryl groups can be further substituted by one or more functional groups including, but not limited to, chemical moieties comprising N, S, O, —NH$_2$, —NHCOCH$_3$, —OH, lower alkoxy (C$_1$-C$_4$), and halo (—F, —Cl, —Br, or —I).

As used herein, the term "substituted aliphatic" refers to an alkane, alkene, alkyne, or alicyclic moiety where at least one of the aliphatic hydrogen atoms has been replaced by, for example, a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such include, but are not limited to, 1-chloroethyl and the like.

As used herein, the term "substituted aryl" refers to an aromatic ring or fused aromatic ring system consisting of at least one aromatic ring, and where at least one of the hydrogen atoms on a ring carbon has been replaced by, for example, a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl and the like.

As used herein, the term "cycloaliphatic" refers to an aliphatic structure containing a fused ring system. Examples of such include, but are not limited to, decalin and the like.

As used herein, the term "substituted cycloaliphatic" refers to a cycloaliphatic structure where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, 1-chlorodecalyl, bicyclo-heptanes, octanes, and nonanes (e.g., nonrbornyl) and the like.

As used herein, the term "heterocyclic" represents, for example, an aromatic or nonaromatic ring containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but not limited to furan, oxirane, 2H-pyran, 4H-pyran, 2H-chromene, and benzofuran. Examples of sulfur-containing heterocyclic rings include, but are not limited to, thiophene, benzothiophene, and parathiazine. Examples of nitrogen containing rings include, but not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted with one or more groups selected from aliphatic, nitro, acetyl (i.e., —C(=O)—CH$_3$), or aryl groups.

As used herein, the term "substituted heterocyclic" refers to a heterocylic structure where at least one of the ring carbon atoms is replaced by oxygen, nitrogen or sulfur, and where at least one of the aliphatic hydrogen atoms has been replaced by a halogen, hydroxy, a thio, nitro, an amino, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to 2-chloropyranyl.

As used herein, the term "electron-rich heterocycle," means cyclic compounds in which one or more ring atoms is a heteroatom (e.g., oxygen, nitrogen or sulfur), and the heteroatom has unpaired electrons which contribute to a 6-π electronic system. Exemplary electron-rich heterocycles include, but are not limited to, pyrrole, indole, furan, benzofuran, thiophene, benzothiophene and other similar structures.

As used herein, the term "linker" refers to a chain containing up to and including eight contiguous atoms connecting two different structural moieties where such atoms are, for example, carbon, nitrogen, oxygen, or sulfur. Ethylene glycol is one non-limiting example.

As used herein, the term "lower-alkyl-substituted-amino" refers to any alkyl unit containing up to and including eight carbon atoms where one of the aliphatic hydrogen atoms is replaced by an amino group. Examples of such include, but are not limited to, ethylamino and the like.

As used herein, the term "lower-alkyl-substituted-halogen" refers to any alkyl chain containing up to and including eight carbon atoms where one of the aliphatic hydrogen atoms is replaced by a halogen. Examples of such include, but are not limited to, chlorethyl and the like.

As used herein, the term "acetylamine" shall mean any primary or secondary amino that is acetylated. Examples of such include, but are not limited to, acetamide and the like.

As used herein, the term "a moiety that participates in hydrogen bonding" as used herein represents a group that can accept or donate a proton to form a hydrogen bond thereby. Some specific non-limiting examples of moieties that participate in hydrogen bonding include a fluoro, oxygen-containing and nitrogen-containing groups that are well-known in the art. Some examples of oxygen-containing groups that participate in hydrogen bonding include: hydroxy, lower alkoxy, lower carbonyl, lower carboxyl, lower ethers and phenolic groups. The qualifier "lower" as used herein refers to lower aliphatic groups (C$_1$-C$_4$) to which the respective oxygen-containing functional group is attached. Thus, for example, the term "lower carbonyl" refers to inter alia, formaldehyde, acetaldehyde. Some nonlimiting examples of nitrogen-containing groups that participate in hydrogen bond formation include amino and amido groups. Additionally, groups containing both an oxygen and a nitrogen atom can also participate in hydrogen bond formation. Examples of such groups include nitro, N-hydroxy and nitrous groups. It is also possible that the hydrogen-bond acceptor in the present invention can be the π electrons of an aromatic ring.

The term "derivative" of a compound, as used herein, refers to a chemically modified compound wherein the chemical modification takes place either at a functional group of the compound or backbone.

As used herein, the term "subject" refers to organisms to be treated by the methods of the present invention. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of a compound of the present invention and optionally one or more other agents) for a condition characterized by bacterial infection.

The term "diagnosed," as used herein, refers to the recognition of a disease by its signs and symptoms (e.g., resistance to conventional therapies), or genetic analysis, pathological analysis, histological analysis, and the like.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "effective amount" refers to the amount of a compound (e.g., a compound of the present invention) sufficient to effect beneficial or desired results. An effective amount can be administered in one or more administrations, applications or dosages and is not limited intended to be limited to a particular formulation or administration route.

As used herein, the term "co-administration" refers to the administration of at least two agent(s) (e.g., a compound of the present invention) or therapies to a subject. In some embodiments, the co-administration of two or more agents/therapies is concurrent. In some embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the terms "purified" or "to purify" refer, to the removal of undesired components from a sample. As used herein, the term "substantially purified" refers to molecules that are at least 60% free, preferably 75% free, and most preferably 90%, or more, free from other components with which they usually associated.

As used herein, the term "modulate" refers to the activity of a compound (e.g., a compound of the present invention) to affect (e.g., to promote or retard) an aspect of cellular function, including, but not limited to, bacterial growth and the like.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., bacterial infection). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In some embodiments, "test compounds" are agents that modulate apoptosis in cells.

DETAILED DESCRIPTION OF THE INVENTION

The present invention relates to chemical compounds, methods for their discovery, and their therapeutic use. In particular, the present invention provides compounds as therapeutic agents in bacterial infections (e.g., Group A Streptococcus and other Streptococcus species).

The widespread occurrence of antibiotic resistance among bacteria is causing increasing concern as a major threat to public health threats. Current antibiotics cause death or growth arrest in the target bacteria. As a result, antibiotic use exerts strong selective pressure to favor antibiotic resistant strains. Novel antimicrobial reagents that suppress pathogen virulence without selecting for antibiotic resistance provide a promising alternative approach for treatment of infectious diseases. Group A Streptococcus (GAS) is an important human pathogen affecting millions of people globally each year. The streptokinase (SK) is a major GAS virulence factor that activates human plasminogen. Streptokinase/plasminogen interaction is a critical factor in GAS pathogenesis. Embodiments of the present invention provide novel antimicrobial reagents for the treatment of GAS infection. In experiments conducted during the course of development of embodiments of the present invention, 55,000 small compounds were screened as inhibitors of SK expression in GAS and 23 hit compounds were identified.

In some embodiments, the compounds or derivatives thereof find use as inhibitors of SK in GAS virulence. In some embodiments, an additional high throughput screen of up to 500,000 more small compounds for SK expression inhibitors is carried out using the NIH Molecular Libraries and Imaging roadmap initiative. A growth based screen is optimized to use a GAS strain with kanamycin resistance gene under control of SK promoter to screen for small compounds that can inhibit kanamycin resistance expression, which serves as lead compounds for SK expression inhibitors. In some embodiments, global effects of compounds on GAS gene expression are analyzed to provide identification of the targets.

In some embodiments, murine GAS infection models are used to analyze the effects of compounds on GAS virulence in vivo. GAS and SK have been shown to interact with the host fibrinolytic system to promote invasion of host tissues. A murine GAS infectious model was used to show that the SK/plasminogen interaction was important for GAS pathogenecity. Based on the data showing that inhibition of SK expression can inhibit GAS virulence without fostering development of antibiotic resistance, a screening strategy to identify antimicrobial reagents against GAS infection was developed. The screen was used to identify 23 small compounds that inhibit SK expression without killing GAS. The present invention is not limited to a particular mechanism. Indeed, an understanding of the mechanism is not necessary to practice the present invention. Nonetheless, it is contemplated that suppressing SK gene (ska) expression in GAS diminishes GAS virulence. Compounds that inhibit ska expression are able to mitigate GAS infection without exerting strong selective pressure for resistance. Such small compounds find use in treating GAS infection and in studying the mechanisms underlying GAS pathogenecity.

The interaction between pathogens and their hosts is a dynamic evolving process. Both genetic and environmental factors play important roles in determining the susceptibility of human populations to bacterial infection. Host defense against bacterial invasion is achieved through a network of tightly regulated interacting genes. The reaction to an infection is a coordinated response involving the immune and inflammatory systems. However, host hemostatic system's involvement is less well appreciated. Recent studies have demonstrated the important roles of plasminogen (Broeseker et al., Microb. Pathog. 1988; 5:19-27; Christner et al., J. Infect. Dis. 1997; 175:1115-1120; D'Costa et al., Methods 2000; 21:165-177; DesJardin et al., Thromb. Res. 1989; 55:187-193; Li et al., J. Infect. Dis. 1999; 179:907-914; Lottenberg et al., Infect. Immun. 1987; 55:1914-1918; Lottenberg et al., J. Infect. Dis. 1992; 166:436-440) and fibrinogen (Li et al., J. Infect. Dis. 1999; 179:907-914; Wang et al., J. Infect. Dis. 1995; 171:85-92; Wang et al., Microb. Pathog. 1995; 18:153-166) in this process.

Binding and activation of plaminogen by bacteria has been shown in a number of pathogens such as Borrelia burgdorferi (Coleman et al., Infect. Immun. 1995; 63:2478-2484; Coleman et al., Cell 1997; 89:1111-1119), Yersinia pestis (Sodeinde et al., Science 1992; 258:1004-1007; McDonough et al., Mol. Microbiol. 1989; 3:767-775; McDonough et al., J. Med. Entomol. 1993; 30:772-780; Sodeinde et al., Infect. Immun. 1988; 56:2743-2748), Escherichia coli, salmonella typhimurium, Neisseria meningitidis and Haemophilis influenzae (Wang et al., J. Infect. Dis. 1995; 171:85-92; Wang et al., Microb. Pathog. 1995; 18:153-166; Boyle et al., Thromb. Haemost. 1997; 77:1-10; Coleman et al., J. Lab Clin. Med. 1999; 134:567-576; Lahteenmaki et al., Microbiol. Rev. 2001; 25:531-552). The fibrinolytic activity of streptococci was first found to be species-specific and dependent on the source of the pathogenic isolate (Tillett et al., J. Exp. Med. 1933; 58:485-502). Streptokinase (SK) is the streptococcal plasminogen activator responsible for this activity (Marcum et al., Comp Biochem. Physiol B 1983; 75:389-394; Nowicki et al., Thromb. Haemost. 1994; 72:595-603; McCoy et al., J. Infect. Dis. 1991; 164:515-521; Schroeder et al., Infect. Immun. 1999; 67:6487-6495). SK has been clinically useful in dissolving acute thromboses underlying myocardial infarction and stroke (Lijnen et al., Thromb. Haemost. 1995; 74:387-390; Metz et al., J. Am. Coll. Cardiol. 1998; 31:1493-1498). The crystal structure of the catalytic domain of human plasmin complexed with SK has been solved (Wang et al., Eur. J. Biochem. 2000; 267:3994-4001). SK can induce a conformational change in the activation pocket of plasminogen by forming a stoichiometric complex with plasminogen, converting plasminogen into an active serine protease without proteolysis. This complex can hydrolytically activate other plasminogen molecules as well. Furthermore, this complex restricts the access of plasmin to its inhibitors α2-antiplasmin (Esmon et al., Nat. Struct. Biol. 1998; 5:933-937). SK can also activate plasminogen both in the presence and absence of fibrin, which makes it distinct from the host plasminogen activators such tissue plasminogen activator (tPA) and urokinase plasminogen activator (uPA) (Reed et al., Proc. Natl. Acad. Sci. U.S.A 1999; 96:8879-8883; Mundada et al., J. Biol. Chem. 2003; 278:24421-24427).

It was previously demonstrated that SK is a key virulence factor for GAS infection and that the interaction between host plasminogen (PLG) and SK is important for GAS pathogenicity (Sun et al., Science 2004; 305:1283-1286). At the site of a local microbial infection, a number of secreted bacterial products, in conjunction with the cascade of cytokines released by host inflammatory cells, induce a vigorous response in the surrounding host vasculature, including high level expression of tissue factor, plasminogen activator inhibitor 1 (PAI-1), and a variety of other prothrombotic factors that trigger the coagulation cascade to form occlusive thrombi (Esmon, Thromb. Res. 2004; 114:321-327; Levi et al., Crit. Care Med. 2002; 30:S220-S224; Levi et al., Cardiovasc. Res. 2003; 60:26-39; Levi et al., Circulation 2004; 109:2698-2704). The present invention is not limited to a particular mechanism. Indeed, an understanding of the mechanism is not necessary to practice the present invention. Nonetheless, it is contemplated that this local thrombosis serves to wall-off the site of infection and limit pathogen invasion and spread. Bacterial plasminogen activators, such as SK, would then function to combat this thrombotic host defense by activating plasmin to dissolve fibrin clots and clear the surrounding vasculature to facilitate bacterial spread (Sun, Physiology (Bethesda.) 2006; 21:281-288).

The genomes of several serotypes of GAS are available (Ferretti et al., Proc. Natl. Acad. Sci. U.S.A 2001; 98:4658-4663; Holden et al., J. Bacteriol. 2007; 189:1473-1477; Nakagawa et al., Genome Res. 2003; 13:1042-1055). Studies of GAS gene regulation have been greatly facilitated by the availability of multiple GAS genome sequences (Kreikemeyer et al., Trends Microbiol. 2003; 11:224-232). Many putative regulatory systems have been deduced from the GAS genome, including 'stand-alone' response regulators and two component systems (TCS) (Kreikemeyer et al., Trends Microbiol. 2003; 11:224-232). 'Stand-alone' regulators are transcriptional regulatory proteins that regulate expression of multiple genes in response to the environment. Two component systems are used by bacteria to sense and respond to environment stimuli. They consist of a membrane-bound sensor and cytoplasmic response regulator. There are, on average, 13 distinct TCSs in GAS (Graham et al., Proc. Natl. Acad. Sci. U.S.A 2002; 99:13855-13860). Only three TCSs have been functionally characterized (Kreikemeyer et al., Trends Microbiol. 2003; 11:224-232). FasBCAX (Fibronectin/fibrinogen binding/hemolytic activity/streptokinase regulator) and CovRS (Control of Virulence genes) are TCSs that have been demonstrated to regulate ska expression (Malke et al., Indian J. Med. Res. 2004; 119 Suppl:48-56; Federle et al., J. Bacteriol. 1999; 181:3649-3657; Kreikemeyer et al., Mol. Microbiol. 2001; 39:392-406). CovRS regulates ska expression negatively (Federle et al., J. Bacteriol. 1999; 181:3649-3657) while FasBCAX is involved in positive regulation of ska expression (Kreikemeyer et al., Mol. Microbiol. 2001; 39:392-406). TCS regulates the expression of a number of genes. For example, it is estimated that CovRS regulates approximately 271 genes which account for 15% of the GAS genome (Graham et al., Proc. Natl. Acad. Sci. U.S.A 2002; 99:13855-13860). The FasBCAX system downregulates genes encoding GAS adhesins (fbp54 and mrp), while upregulating genes encoding secreted GAS virulence factors (sagA and ska) (Kreikemeyer et al., Mol. Microbiol. 2001; 39:392-406). Given the limited knowledge of GAS gene transcription regulation, it is likely that the ska gene is also under the control of other unknown TCSs and regulators.

The emergence of antibiotic resistance is an urgent medical problem worldwide. Many of the current antibiotics are derivatives of parental compounds that were developed more than forty years ago and target a small set of proteins essential for bacterial survival, such as cell wall formation, and synthesis of bacterial DNA, RNA, lipid and protein. As a result, antibiotic resistant strains have been favored by selective pressure (Martinez et al., Clin. Microbiol. Rev. 2002; 15:647-679). A number of other factors, including inappropriate and excessive use of antibiotics, have contributed to the emergence of pathogens that are highly resistant to most currently available antibiotics (Alanis, Arch. Med. Res. 2005; 36:697-705; Bax et al., Int. J. Antimicrob. Agents 2000; 16:51-59; Norrby et al., Lancet Infect. Dis. 2005; 5:115-119; Silver, Nat. Rev. Drug Discov. 2007; 6:41-55). Current antimicrobial development is largely limited to improving the efficacy of existing antibiotics.

There is thus a great need for the development of novel strategies to combat infectious diseases. The inhibition of pathogen virulence without introducing selection for antibiotic resistance holds tremendous promise as an alternative to traditional antibiotic strategies. Accordingly, in some embodiments, the present invention provides antimicrobial agents that attenuate the virulence of pathogens without inhibiting the growth of the pathogens. Furthermore, it is contemplated that this new class of antimicrobials acts cooperatively or synergistically with conventional antibiotics, since they act through an independent mechanism.

I. Inhibitors

As described in more detail below, embodiments of the present invention provide compounds that specifically inhibit bacterial (e.g., Group A *Streptococcus* (GAS) or other related *streptococcus* species) pathogenicity. In some embodiments, the present invention provides compounds that specifically inhibit streptokinase (SK) from GAS.

In some embodiments, the compound has the structure

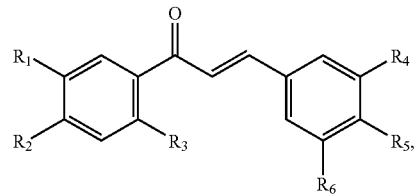

wherein R1 and R2 are selected from H, alkyl or O-alkyl, $R_3$ is an O-alkyl, $R_3$ is H or O-alkyl and, $R_4$, $R_5$ and R6 are an O-alkyl. In some embodiments, the compound has the structure

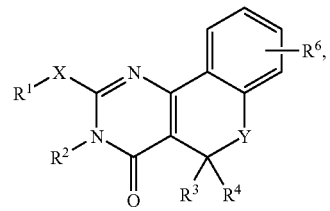

wherein $R^1$ is a C1-C6 alkyl, optionally substituted with CN, $OR^7$, $NR^7_2$, $CO_2R^7$, $CONHR^7$, heteroaryl, Ph, $R^2$ is a C1-C6 alkyl or alkenyl $R^3$ and $R^4$ are, independently, H, a C1-C6 alkyl or joined in a cycloalkyl ring of 3-7 carbons, and $R^6$ is H or one or more standard aryl substituents and $R^7$=H or a C1-C3 alkyl.

In some embodiments, the compound is

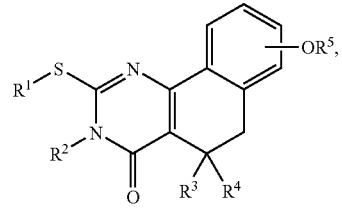

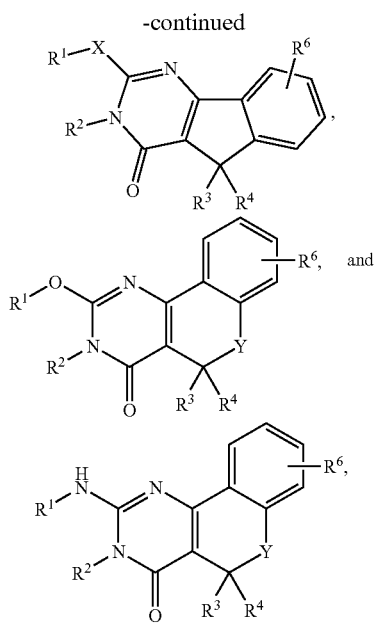

wherein X is S, O or NH, Y is $(CH_2)_n$ or $CH-R^8$, $R^1$ is a C1-C6 alkyl, optionally substituted with CN, $OR^7$, $NR^7_2$, $CO_2R^7$, $CONHR^7$, heteroaryl, Ph, $R^2$ is a C1-C6 alkyl or alkenyl $R^3$ and $R^4$ are, independently, H, a C1-C6 alkyl or joined in a cycloalkyl ring of 3-7 carbons $R^5$ is C1-C6 alkyl, optionally substituted with CN, $OR^7$, $NR^7_2$, $CO_2R^7$, $CONHR^7$, heteroaryl, Ph, $SO_2R^7$, $NHCOR^7$, $SO_2NHR^7$, $OCOR^7$, $R^6$ is H or one or more standard aryl substituents and $R^7$=H or a C1-C3 alkyl, $R^8$ is a $C_1$-$C_6$ alkyl and n=0 or 1.

For example, in some embodiments, the present invention provides streptokinase inhibitors selected from, for example, those described in Tables 1 and 2. In other embodiments, SK inhibitors are identified in additional screening assays (e.g., those described herein). In yet other embodiments, the present invention provides derivatives, mimetics, analogs, sterioisomers, analogs, etc. of the identified compounds.

The present invention also provides methods of modifying and derivatizing the compositions of the present invention to increase desirable properties (e.g., binding affinity, activity, solubility and the like), or to minimize undesirable properties (e.g., nonspecific reactivity, toxicity, and the like). The principles of chemical derivatization are well understood. In some embodiments, iterative design and chemical synthesis approaches are used to produce a library of derivatized child compounds from a parent compound. In some embodiments, rational design methods are used to predict and model in silico ligand-receptor interactions prior to confirming results by routine experimentation.

The present invention is not limited to the targeting of sk from GAS. It has been shown that fasA gene exist among several streptococci that are closely related to GAS such as *S. dysgalactiae*, *S. equi* and *S. uberis* (Malke et al., Indian J. Med. Res. 2004; 119 Suppl:48-56). Homologous FasBCAX operons are detected in *S. equi* and *S. uberis* genome while homologous FasCAX operon exists in *S. dygalactiae* which lacks fasB (Steiner et al., Infect. Immun. 2002; 70:3627-3636). Therefore, in some embodiments, the present invention provides methods of targeting other pathogenic streptococci and provides compounds that have broad spectrum therapeutic effects in multiple streptococci. Examples include, but are not limited to, *S. dysgalactiae* (Group C or G streptococci) causes bacteremia and streptococcal toxic shock-like syndrome (Hashikawa et al., J. Clin. Microbiol. 2004; 42:186-192; Pinho et al., J. Clin. Microbiol. 2006; 44:841-846; Sylvetsky et al., Am. J. Med. 2002; 112:622-626). *S. equi* causes strangles, one of the most feared infectious diseases in horses (Harrington et al., Microbes. Infect. 2002; 4:501-510). *S. uberis* is the main cause of bovine mastitis (Bradley, Vet. J. 2002; 164:116-128; Leigh, Vet. J. 1999; 157:225-238).

II. Pharmaceutical Compositions, Formulations, and Exemplary Administration Routes and Dosing Considerations Exemplary embodiments of various contemplated medicaments and pharmaceutical compositions are provided below.

A. Preparing Medicaments

The compounds of the present invention are useful in the preparation of medicaments to treat bacterial (e.g., GAS) infection. The methods and techniques for preparing medicaments of a compound are well-known in the art. Exemplary pharmaceutical formulations and routes of delivery are described below.

One of skill in the art will appreciate that any one or more of the compounds described herein, including the many specific embodiments, are prepared by applying standard pharmaceutical manufacturing procedures. Such medicaments can be delivered to the subject by using delivery methods that are well-known in the pharmaceutical arts.

B. Exemplary Pharmaceutical Compositions and Formulation

In some embodiments of the present invention, the compositions are administered alone, while in some other embodiments, the compositions are preferably present in a pharmaceutical formulation comprising at least one active ingredient/agent (e.g., GAS SK inhibitors), as defined above, together with a solid support or alternatively, together with one or more pharmaceutically acceptable carriers and optionally other therapeutic agents. Each carrier should be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In some embodiments, the active ingredient is presented as a bolus, electuary, or paste, etc.

In some embodiments, tablets comprise at least one active ingredient and optionally one or more accessory agents/carriers are made by compressing or molding the respective agents. In some embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternatively embodiments, topical formulations comprise patches or dressings such as a bandage or adhesive plasters impregnated with active ingredient(s), and optionally one or more excipients or diluents. In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in an known manner. This phase typically comprises an lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. It some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate.

Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

C. Exemplary Administration Routes and Dosing Considerations

Various delivery systems are known and can be used to administer a therapeutic agent (e.g., GAS SK inhibitor) of the present invention, e.g., encapsulation in liposomes, microparticles, microcapsules, receptor-mediated endocytosis, and the like. Methods of delivery include, but are not limited to, intra-arterial, intra-muscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

The agents identified herein as effective for their intended purpose can be administered to subjects or individuals susceptible to or at risk of developing GAS infection and conditions correlated with this. When the agent is administered to a subject such as a mouse, a rat or a human patient, the agent can be added to a pharmaceutically acceptable carrier and systemically or topically administered to the subject. To determine patients that can be beneficially treated, a tissue sample is removed from the patient and the cells are assayed for sensitivity to the agent.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

D. Exemplary Co-Administration Routes and Dosing Considerations

The present invention also includes methods involving co-administration of the compounds described herein with one or more additional active agents. Indeed, it is a further aspect of this invention to provide methods for enhancing prior art therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or other treatments may each be administered using different modes or different formulations.

The agent or agents to be co-administered depends on the type of condition being treated. For example, when the condition being treated is bacterial infection, the additional agent can be a known antibiotic. The additional agents to be co-administered, such as antibacterial, immunosuppressant, anti-inflammatory, and can be any of the well-known agents in the art, including, but not limited to, those that are currently in clinical use.

III. Drug Screens

In some embodiments of the present invention, the compounds of the present invention, and other potentially useful compounds, are screened for their biological activity (e.g., ability to block SK GAS).

In some embodiments, structure-based virtual screening methodologies are contemplated for identifying GAS SK inhibitors. For example, in some embodiments, molecular modeling is used to identify inhibitors. In some embodiments, modeling is used to identify compounds that inhibit the expression of SK from GAS.

In some embodiments, compounds are screened in cell culture or in vivo (e.g., non-human or human mammals) for their ability to inhibit SK. In some embodiments, screens detecting expression or inhibition of expression of downstream signaling molecules.

In some embodiments, the screening methods described in the experimental section below are utilized. For example, in some embodiments, high throughput screens in bacteria are performed. In one embodiments, high throughput screening is performed in E. coli utilizing a antibiotic resistance or other marker gene under the control of GAS ska promoters. In other embodiments, a high throughput assay is performed in GAS that comprise a marker gene (e.g., antibiotic resistance) under the control of the ska promoter. Compounds are screened for their ability to inhibit the growth of the reporter GAS cells. In some embodiments, compounds are screened for their ability in kill or inhibit the growth of GAS. In some embodiments, dose response assays are performed.

In some embodiments, compounds indentified in the bacterial screening assays above are further screened in animals. For example, in some embodiments, a mouse model of GAS infection is used in screening assays.

EXAMPLES

The following examples are provided to demonstrate and further illustrate certain embodiments of the present invention and are not to be construed as limiting the scope thereof.

Example 1

Generation of Transgenic Mice Expressing Human Plasminogen

Mice are generally very resistant to infection by human GAS. This remarkable species-specificity has been proposed to result from the species-specific interaction between SK secreted by GAS and the preferred host's plasminogen, the central proteinase in the fibrinolytic system (Marcum et al., Comp Biochem. Physiol B 1983; 75:389-394; Nowicki et al., Thromb. Haemost. 1994; 72:595-603; McCoy et al., J. Infect. Dis. 1991; 164:515-521; Schroeder et al., Infect. Immun. 1999; 67:6487-6495). In order to study the role of the fibrinolytic system in GAS infection, transgenic mice expressing the human plasminogen protein were generated using a Bacteria Artificial Chromosome (BAC) transgenic technique. The BAC modification method was adapted from Yang et al (Yang et al., Nat. Biotechnol. 1997; 15:859-865), and had been used to successfully generate liver-specific factor V expression (Sun et al., Blood 2003; 102:2856-2861).

The coding region of the murine albumin (Malb) gene in the BAC was replaced with the human plasminogen (PLG) cDNA and the modified BAC was used to generate transgenic mice. Offspring were screened by PCR and two independent Malbplg BAC founders were identified. The two Malbplg lines exhibit highly liver-specific expression, with no expression detected in other tissues by RT-PCR. The Malbplg1 Tg+ line exhibited levels of expression corresponding to 17% of human plasma (16.7±1.78) while a level of less than 1% human PLG was expressed in the Malbplg2 line. Previous studies of plasminogen null mice (Plg−/−) showed prothrombotic morbidity (Bugge et al., Genes Dev. 1995; 9:794-807; Ploplis et al., Circulation 1995; 92:2585-2593).

In order to test whether the human plasminogen protein expressed from the Malbplg1 transgene can compensate for the function of mouse plasminogen in vivo, the Malbplg1 Tg+ line was crossed to Plg+/− for two generations to generate Tg+Plg−/− offspring. Tg+Plg−/− were then analyzed to examine the extent of phenotypic rescue by the human plasminogen transgene. Histological examination of liver tissues from three 10 weeks old Plg−/− mice revealed similar fibrin deposits as previously reported (Bugge et al., supra; Ploplis et al., supra). However, liver tissues from three Plg+ and five Tg+Plg−/− littermates revealed little or no fibrin deposition (FIG. 1A-D). These observations demonstrate that human plasminogen can rescue fibrin deposition caused by plasminogen deficiency, and that human plasminogen expressed from the Malbplg1 transgene is able to compensate for the function of mouse plasminogen in vivo (Sun et al., Science 2004; 305:1283-1286).

Example 2

Human Plasminogen Transgenic Mice are Susceptible to GAS Infection

Figure 2:
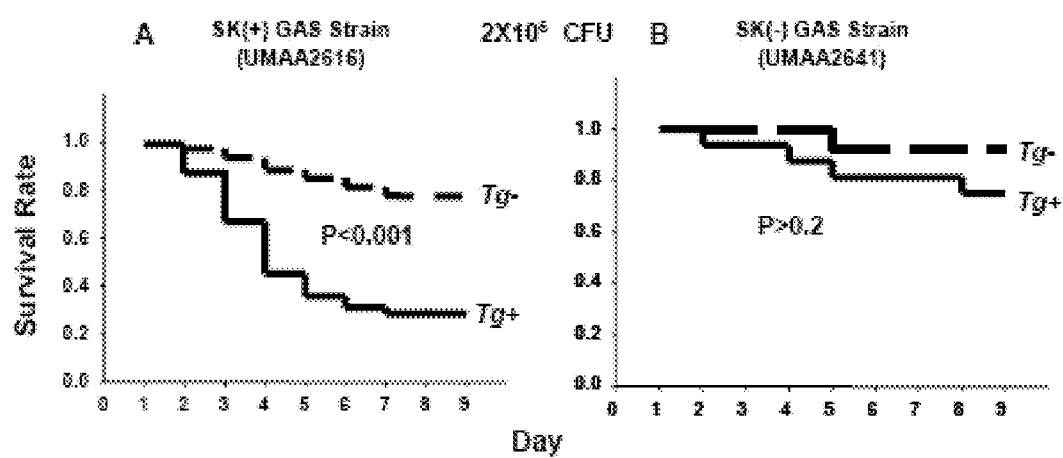
FIG. 2 shows SK/PLG interaction is critical for GAS pathogenesis.

The difference in susceptibilities between wild-type C57BL6/J mice (Tg−) and mice carrying the Malbplg1 transgene (Tg+) to GAS infection was tested. Using a hypervirulent streptococcal strain (UMAA2616/SK(+)GAS) at a dose of $2 \times 10^5$ colony forming unit (CFU), administered subcutaneously, a 20% mortality was observed in control Tg− mice at 9 days while addition of human plasminogen directed by the Malbplg1 transgene markedly increased the mortality in C57BL6/J mice to 70% at 9 days (FIG. 2A). Similar results were obtained with a GAS strain with wild-type virulence, MGAS166. These results demonstrate an important role for human plasminogen in the pathogenecity of human GAS isolates in this mouse model, a function that is not provided by mouse plasminogen.

The role of the SK/PLG interaction in GAS pathogenesis was also tested by injecting Tg+ mice with a streptokinase null GAS variant (UMAA2641/SK(−)GAS). The increased susceptibility of Tg+ mice to the wild-type streptococcal isolate SK(+)GAS was largely abrogated after deletion of the streptokinase gene (FIG. 2B). These results demonstrate that SK is a key determinant for host-specificity of streptococcal infection.

Example 3

SK Hijacks the Host Fibrinolytic System to Facilitate GAS Invasion

Figure 3:
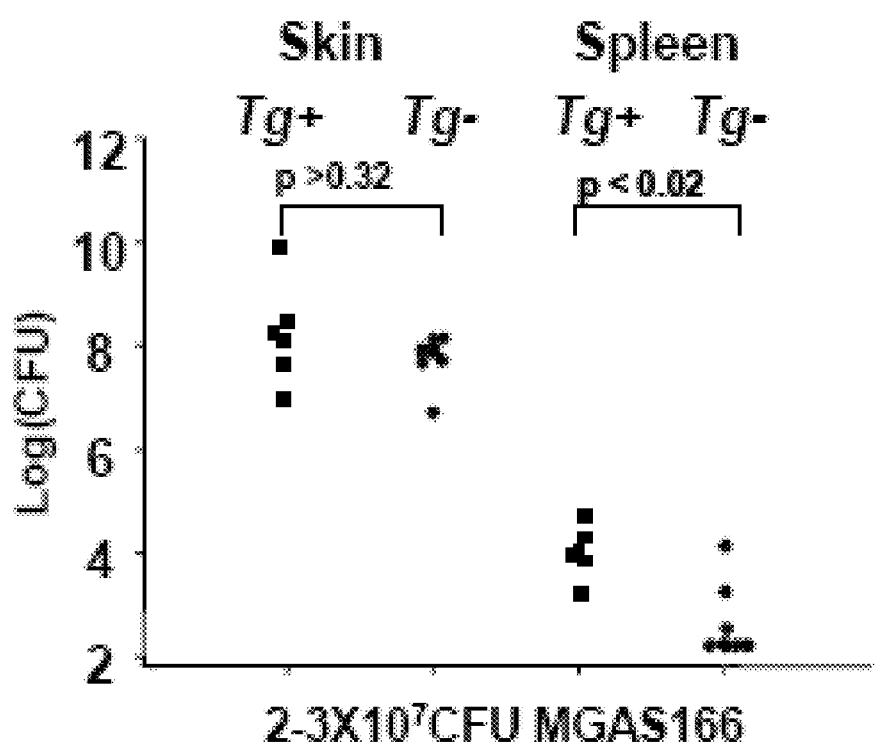
FIG. 3 shows systemic spread of GAS.
Figure 4:
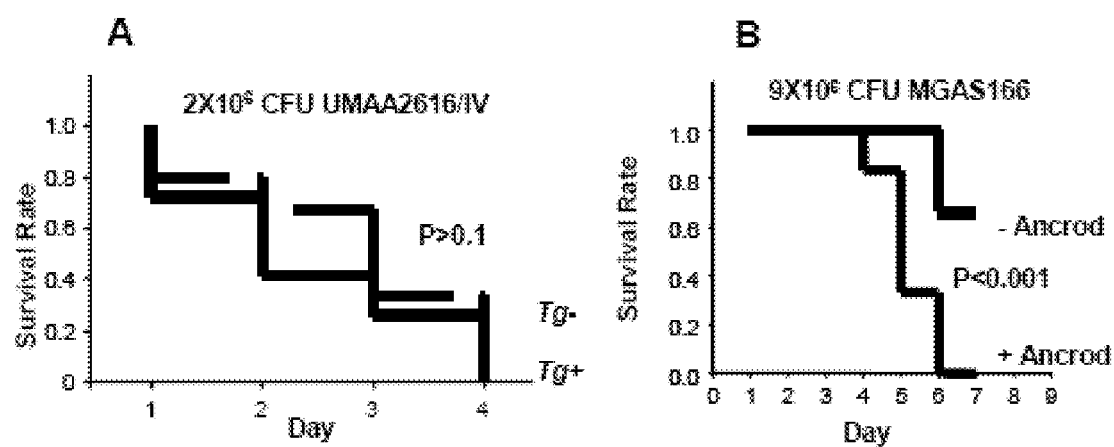
FIG. 4 SK facilitates GAS systemic invasion.

Streptococcal dissemination was also assessed by counting the number of bacteria colonies recovered from spleens of human plasmingen Tg+ and Tg− mice after infection. The bacterial count was significantly higher in the spleens of Tg+ mice than in Tg− mice (FIG. 3), indicating that there was more systemic spread of bacteria in Tg+ mice than in Tg− mice. Based on these data, it was hypothesized that local vascular thrombosis resulting from bacterial infection serves to wall off the site of infection and limit pathogen invasion and spread and that SK hijacks the host fibrinolytic system to overcome this thrombotic barrier for GAS invasion. The route of inoculation was altered and it was found that the resistance of mice to GAS invasion in the absence of human plasminogen was lost with direct introduction of bacteria into the circulation. No difference in survival was observed between Tg+ and Tg− mice following intravenous GAS administration (FIG. 4A).

To further test this hypothesis, the role of fibrinogen in host defense against streptococcal infection was also examined. The plasma fibrinogen level in wildtype C57BL6/J mice was decreased by 60% upon administration of the snake venom ancrod. Administration of Ancrod resulted in a markedly increased susceptibility to streptococcal infection (FIG. 4B).

Example 4

Decreasing Thrombin Generation Increases Host Susceptibility to GAS Infection

Figure 5:
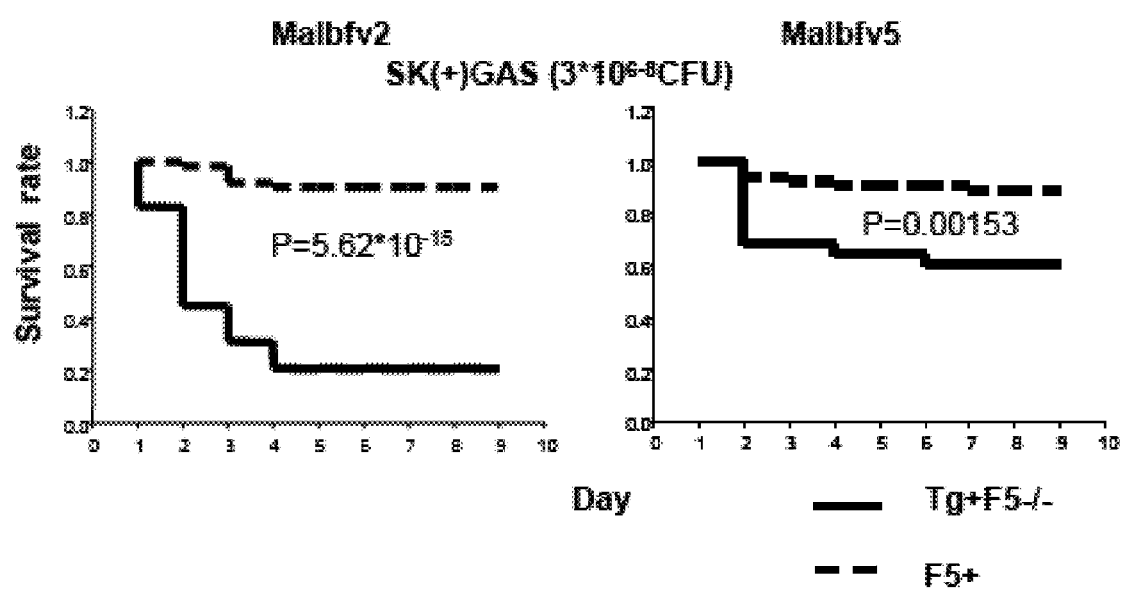
FIG. 5 shows reduction of plasma FV level increases host susceptibility

Mice genetically modified to have coagulation defects were used to test the role of thrombosis in host defense. Factor V (FV) is a central regulator of hemostasis, serving as an essential component of the prothombinase complex and as a key target of the natural anticoagulant activated protein C (APC) (Mann et al., Blood 2003; 101:20-30; Kisiel et al., Biochemistry 1977; 16:5824-5831; Rosing et al., Thromb. Haemost. 1997; 78:427-433; Guinto et al., J. Biol. Chem. 1984; 259:13986-13992). As a result, FV plays a critical role in thrombin generation and local thrombosis formation. The effect of FV level on host thrombotic defense against GAS infection was tested. Mice with decreased level of plasma and platelet FV have been generated previously (Sun et al., Blood 2003; 102:2856-2861). These mice (Tg+F5−/−) have the F5 gene expressed from tissue specific transgenes in the FV null background. One line of mice (Malbfv2) expresses approximately 15% plasma FV with no detectable platelet FV expression. Another line of mice (Malbfv5) expresses about 45% plasma FV with undetectable level of platelet FV. If local vascular thrombosis formation plays a critical role in host defense against GAS systemic invasion, decreased thrombin generation in these mice should render them more susceptible to GAS systemic invasion. As a result, Malbfv2 and Malbfv5 mice are excellent models to study the role of coagulation in GAS infection. Consistent with the hypothesis that decreasing local vascular thrombosis formation weakens host defense against GAS invasion, FV-deficient mice demonstrated marked increase in susceptibility to SK(+)GAS infection compared to their sibling controls, which included both F5+/+ and F5+/− mice (FIG. 5). No significant difference in GAS susceptibility was observed between F5+/+ and F5+/− mice. As a result, they were grouped together as control (F5+). A steep dependence of mortality on plasma FV level was observed as manifested by the difference of susceptibilities between Malbfv2 and Malbfv5 (FIG. 5) mice to GAS infection, strongly supporting the hypothesis that thrombin generation plays a critical role in host defense against GAS infection. Malbfv5 mice are also more susceptible to SK(+) GAS infection than F5+/− mice, even though they have 45% level of plasma FV which is similar to F5+/− mice's plasma FV level (50%). This observation shows that platelet FV is also important for host hemostasis and defense against GAS infection. Enhanced susceptibility of FV-deficient mice to GAS infection could be mediated not only by a reduction in fibrin formation, but also by disruption of thrombin signaling via protease-activated receptors (PARs) (Coughlin, Nature 2000; 407:258-264).

Example 5

Decreasing Fibrinogen Level Increases Host Susceptibility to GAS Infection

Figure 6:
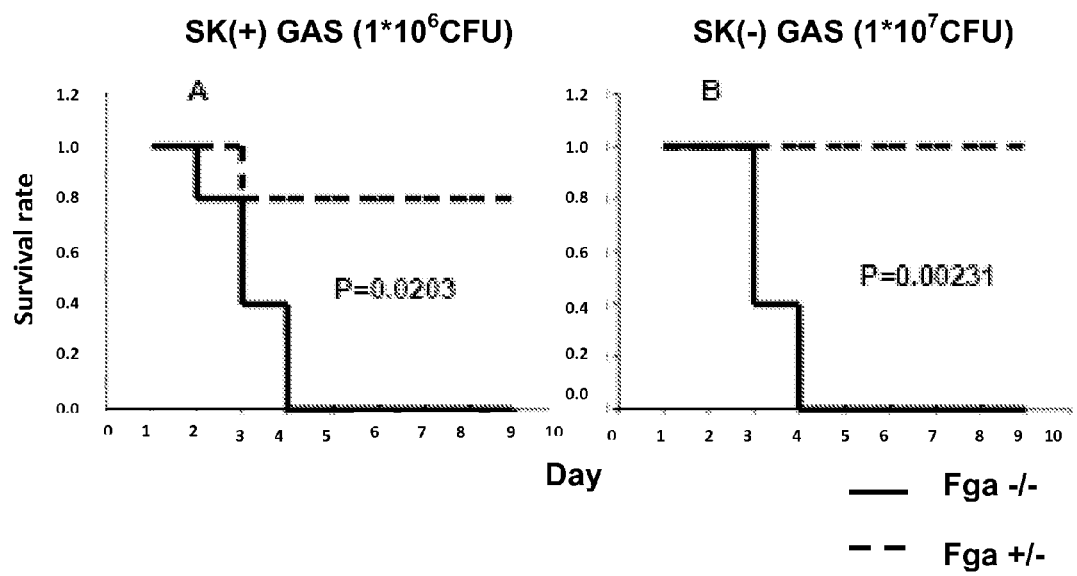
FIG. 6 shows that fibrinogen plays important role in host defense.

It has been proposed that SK binding to fibrinogen is a necessary step to initiate the first stage of bacterial invasion, with fibrinogen forming a trimolecular complex with SK and plasminogen that binds to GAS to localize plasmin formation at the GAS-host tissue interface (Boyle et al., Thromb. Haemost. 1997; 77:1-10; Boyle et al., Methods 2000; 21:99-102). Thus, the function of fibrinogen in GAS infection may be twofold, with fibrinogen binding SK and plasminogen to initiate bacterial invasion, but later blocking bacterial spread through vascular occlusion. Mice that are deficient in fibrinogen have been generated by knock out the fibrinogen Aα chain gene (Suh et al., Genes Dev. 1995; 9:2020-2033). Fibrinogen-deficient mice were used to test the relative importance of the SK/fibrinogen interaction in the initial stage of bacterial invasion versus the subsequent role of fibrinogen in containing bacterial spreading. Fga−/− mice are highly susceptible to both SK(+)GAS and SK(−)GAS infection than Fga+/− controls (FIG. 6). These observations show that fibrinogen is not an absolute requirement for the initiation of GAS infection and the proposed role of local vascular thrombosis, which is dependent on fibrinogen, in host defense more than counterbalances any effect of fibrinogen deficiency on the initiation phase.

Figure 7:
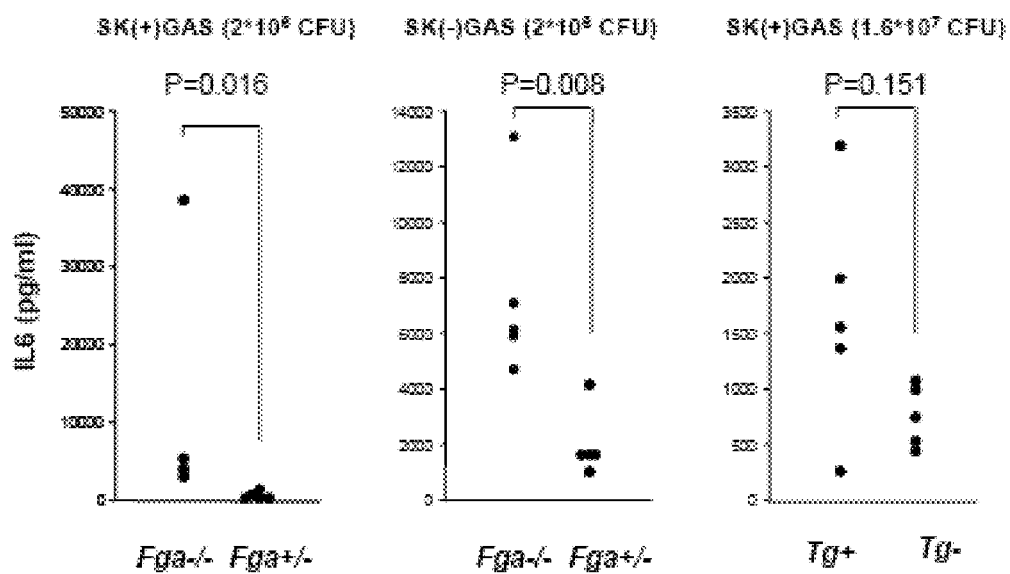
FIG. 7 shows IL-6 is induced in GAS infection.

In addition to fibrinogen's role in forming fibrin clots in blood coagulation, fibrinogen also plays important roles in inflammation reaction (Flick et al., Exp. Biol. Med. (Maywood.) 2004; 229:1105-1110; Flick et al., J. Clin. Invest 2004; 113:1596-1606). Ten cytokine markers of Fga−/− mouse plasma were measured to test whether lack of fibrinogen affects the inflammation reaction of the host by the mouse coagulation laboratory. Fga−/− mice have significantly increased IL-6 level in their plasma comparing to Fga+/− controls when infected by either SK(+)GAS or SK(−)GAS strains (FIG. 7) when infected by SK(+)GAS. A trend of increased IL6 level was also observed in human plasminogen transgenic mice infected with SK(+)GAS comparing to control mice, indicating IL6 as a prognostic biomarker for host response to GAS infection (FIG. 7).

Example 6

Establish Growth-Based Turbidometric Screening Strategy in E. coli for Screening SK Expression Inhibitor An in vivo screen in bacteria for a potentially novel antibiotic activity against GAS was performed. Based on the role of SK in GAS pathogenecity, chemical compounds that specifically reduce the expression of bacterial ska, without interfering with bacterial viability were identified. An E. coli strain (SK-Ecoli) was constructed by transforming E. coli with a plasmid containing a kanamycin resistance gene under the control of GAS ska promoter. A control strain (SKCtr1) was constructed by transforming E. coli with a plasmid containing a kanamycin resistance gene under control of an independent promoter.

Figure 8:
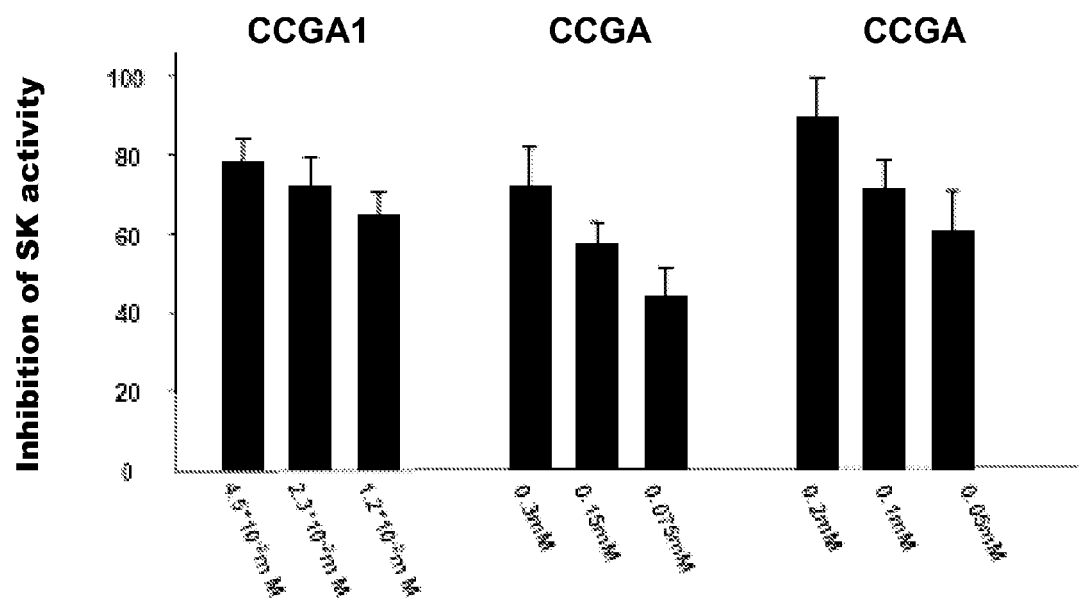
FIG. 8 shows three compounds that inhibit ska expression.
Figure 9:
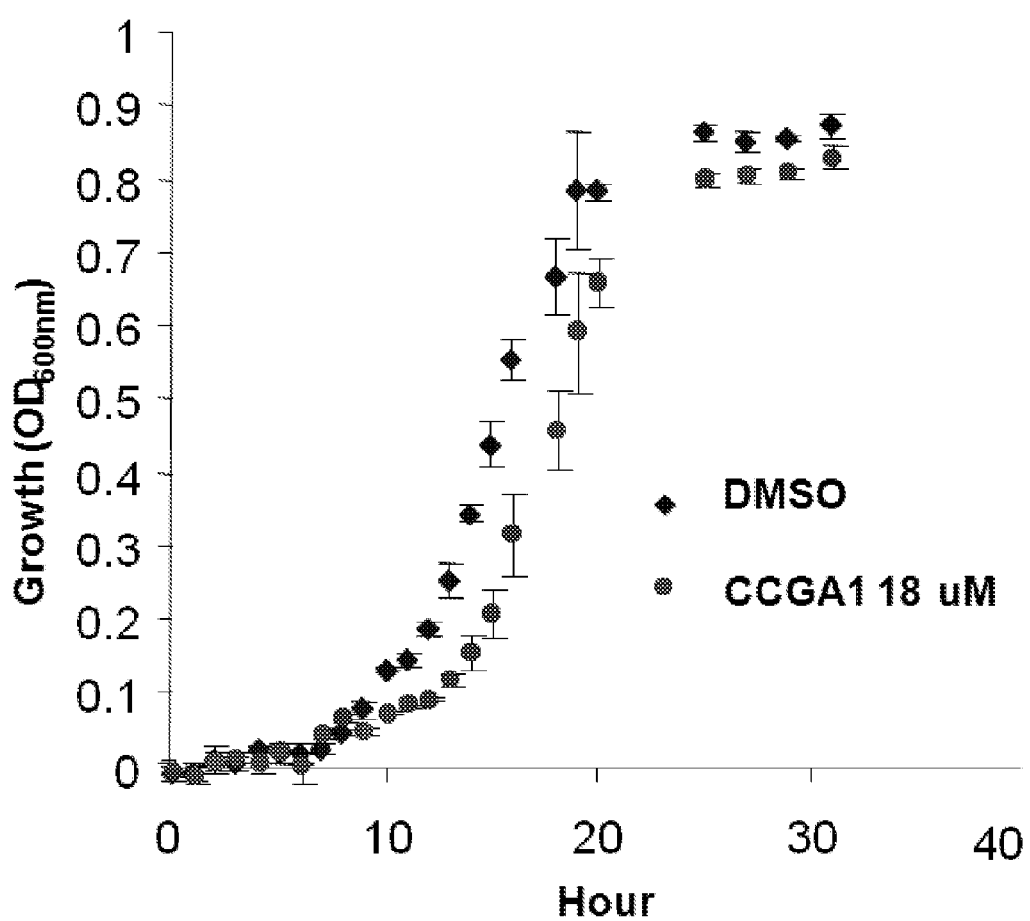
FIG. 9 shows the effect of CCGA1 on GAS Growth.

35,000 small compounds from Chembridge, Chemdiv as well as a natural compound library from Dr. David Sherman were screened in a 384 well format. Compounds that inhibited E. coli growth more than SK-Ctrl (>2 fold difference) were selected for dose-response test. 170 hits were identified (>3SD growth inhibition of SK-Ecoli). 70 were selected as potential specific inhibitors of SK promoter (>2 fold more inhibition of SK-Ecoli growth than SK-Ctrl growth). SK-Ecoli and SKCtr1's dose response relationship with these compounds were then examined. Fourteen compounds out the 70 demonstrated consistent more inhibition in SK-Ecoli than SK-Ctrl in the dose response experiments. Seven compounds out of the 14 potential specific inhibitors have been tested for inhibition of ska expression in SK(+)GAS using chromogenic substrate 2403 (Diapharma group Inc., West Chester, Ohio) according to the manufacturer's instruction. Three compounds demonstrated inhibition of SK expression in SK(+)GAS in a dose-dependent manner (FIG. 8). Compound CCGA1 was tested for its effect on SK(+)GAS growth (FIG. 9). CCGA1 delayed the log phase of bacteria growth without significantly inhibiting its replication.

Example 7

Figure 10:
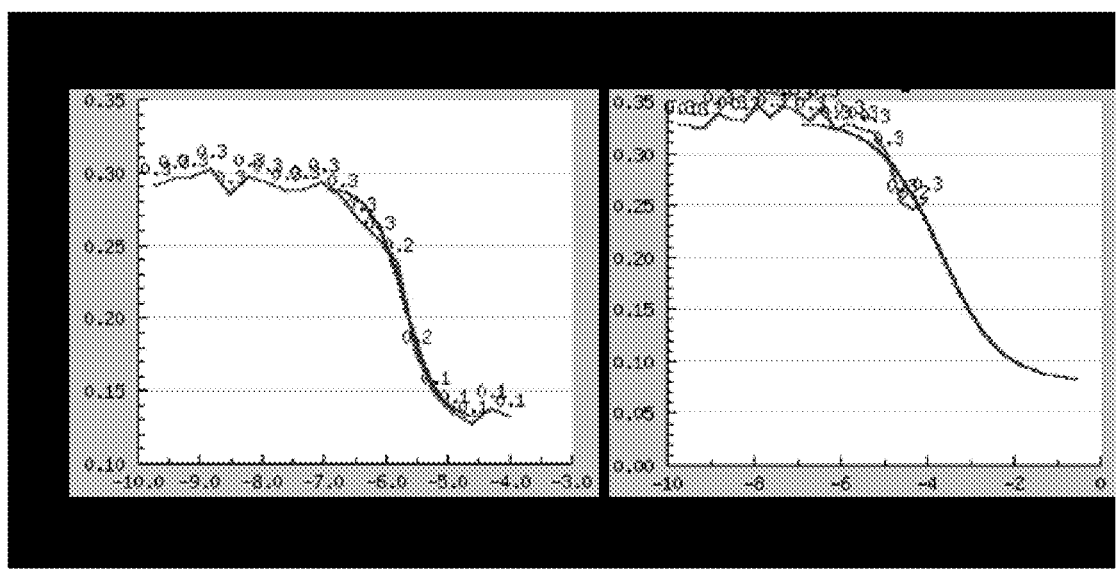
FIG. 10 shows effects of compounds on SKkanGAS and SK(−) GAS.

Establish Growth-Based Turbidometric Screening Strategy in Gas for Screening SK Expression Inhibitors A GAS strain was generated to have kanamycin resistance gene under the control of ski promoter to be used to screen for SK inhibitors. A transgenic GAS has been generated in SK(+) GAS host so that kanamycin resistance gene is driven by ska promoter in an extrachromosomal plasmid. The engineered GAS strain (SKKanGAS) was also kanamycin resistant. This kanamycin resistance gene in SK(−)GAS strain is within the omega-Km2 element whose promoter is independent of ska promoter (Khil et al., J. Infect. Dis. 2003; 188:497-505; Ringdahl et al., J. Biol. Chem. 1998; 273:6424-6430). As a result, SK(−)GAS can serve as a control in the screen for SK promoter to weed out compounds that inhibit GAS growth or interfere with kanamycin resistance protein function. A total of 55,000 small compounds have been screened to identify compounds that demonstrate more growth inhibition of SKKanGAS than SK(−)GAS. A cutoff criterion was set to select compounds that can inhibit 50% growth in SKKanGAS while inhibiting less than 10% growth in SK(−)GAS. A total of 95 compounds met this criterion. As a result, these compounds were chosen for dose response assays and pIC50 of growth inhibition of each hit compound was then estimated. 61 compounds have pIC50 of SKKanGAS strain inhibition less than −4.5. Among these compounds, 20 compounds whose IC50s for SKKanGAS inhibition was more than 10-fold lower than IC50s for SK(−)GAS inhibition were selected for future testing. An example is given as FIG. 10.

Example 8 ska Expression Inhibitors

Figure 11:
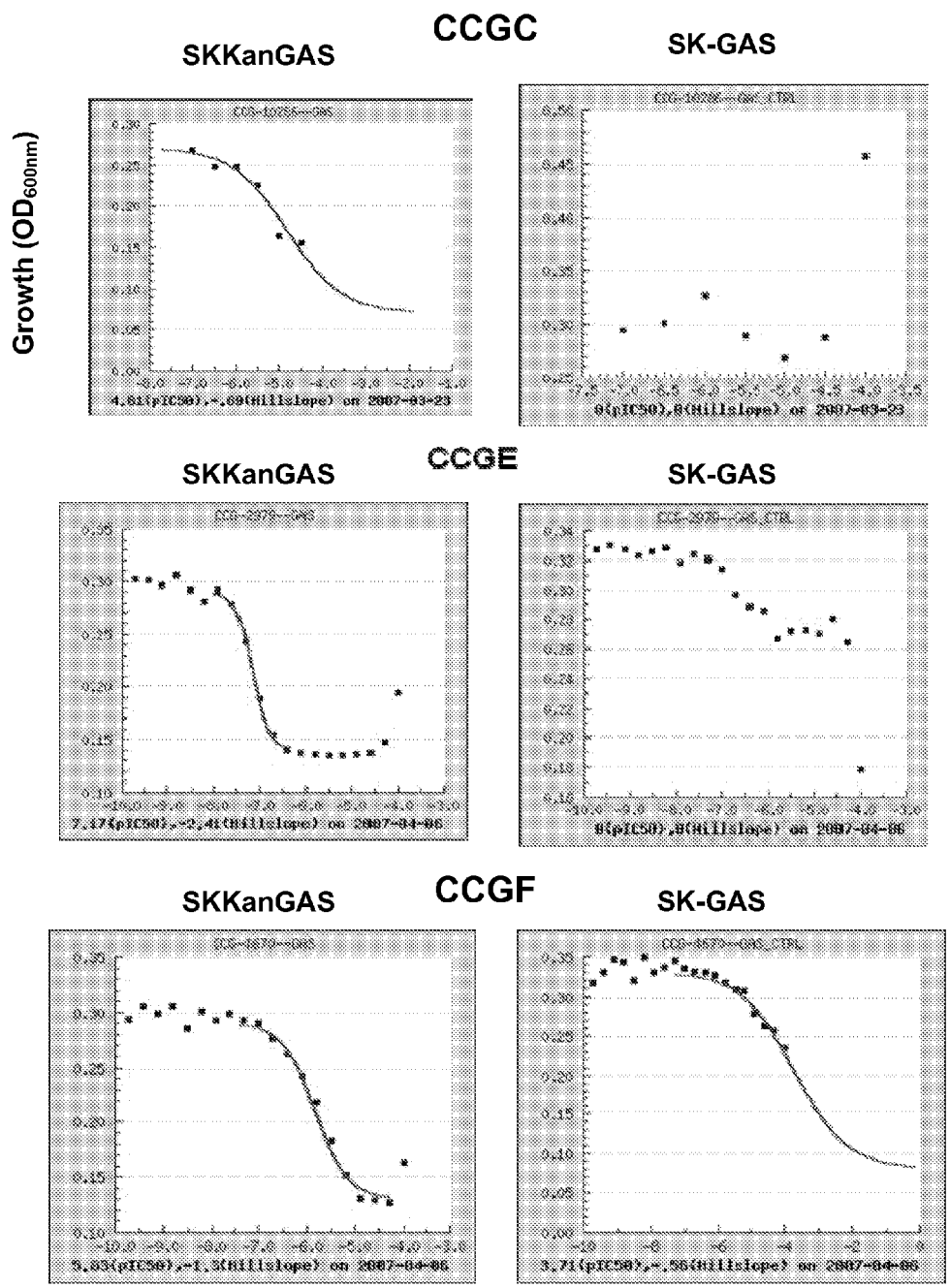
FIG. 11 shows the effects of selected small compounds (CCGC, CCGE and CCGF) on SKKanGAS and SK-GAS. The three compounds show specific inhibition of SKKan-GAS growth under kanamycin selection, consistent with specific inhibition of the ska promoter.
Figure 12:
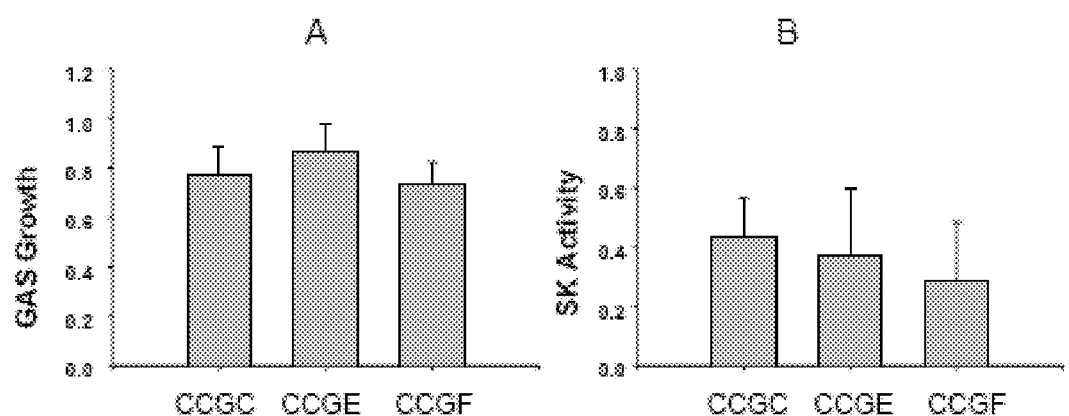
FIG. 12 shows effects of small compounds CCGC (2.5 µM), CCGE (2.9 µM) and CCGF (2.7 µM) on GAS growth and SK expression. A) GAS growth as measured by OD600 nm of overnight culture (the OD600 nm of control GAS grown in DMSO vehicle alone is defined as 1.0). B) Normalized SK activity (SK activity of culture media divided by OD600 nm, then normalized to the value for DMSO treated GAS).

The effects of 10 hit compounds out of the 23 identified were further tested by dose response assays. Several examples are shown in FIG. 11. In order to verify data derived from the original stock of small compound library, fresh samples of the 10 new hit compounds were purchased from commercial suppliers and subjected to confirmatory screening. These compounds were tested for inhibition of ska expression by measuring SK activity in supernatants of GAS exposed to the test compound or control vehicle alone (DMSO). SK(+)GAS were cultured with hit compounds at a dose range of 10 nM to 100 μM at 37° C. for 16-20 hours. Supernatants of SK(+)GAS cultures were measured for SK activity using chromogenic substrate 2403 (Diapharma group Inc., West Chester, Ohio), according to the manufacturer's instruction and simultaneously monitored for nonspecific effects on GAS growth by measuring OD600 nm. Three out of 10 compounds tested demonstrated more than 50% inhibition of SK activity, with less than 30% inhibition of GAS growth (FIG. 12).

Table 1 shows exemplary compounds.

TABLE 1

| Name | Structure |
| --- | --- |
| CCGC | (structure) |
| CCGE | (structure) |
| CCGF | (structure) |
| CCGE2 | (structure) |
| 1S-22207 | (structure) |
| AK-968/ 12713103 | (structure) |
| 1S-26137 | (structure) |
| 1S-30398 | (structure) |
| CCG102493 | (structure) |

TABLE 1-continued

| Name | Structure |
|---|---|
| 1S-25203 | [Structure: Ph—CH₂—S-substituted quinazolinone with N-CH₂-CH=CH₂ and gem-dimethyl] |
| CCGEF5 | [Structure: chalcone with 4-methyl on one ring and 3,4,5-trimethoxy on other ring] |
| CCGF6 | [Structure: chalcone with 3,4,5-trimethoxy on one ring and 3,4-dichloro on other ring] |
| CCGE7 | [Structure: chalcone with 4-methoxy on one ring and 3,4,5-trimethoxy on other ring] |

Example 9

Efficacy of Hit Compounds in the Human Plasminogen Transgenic Mouse Model

Figure 13:
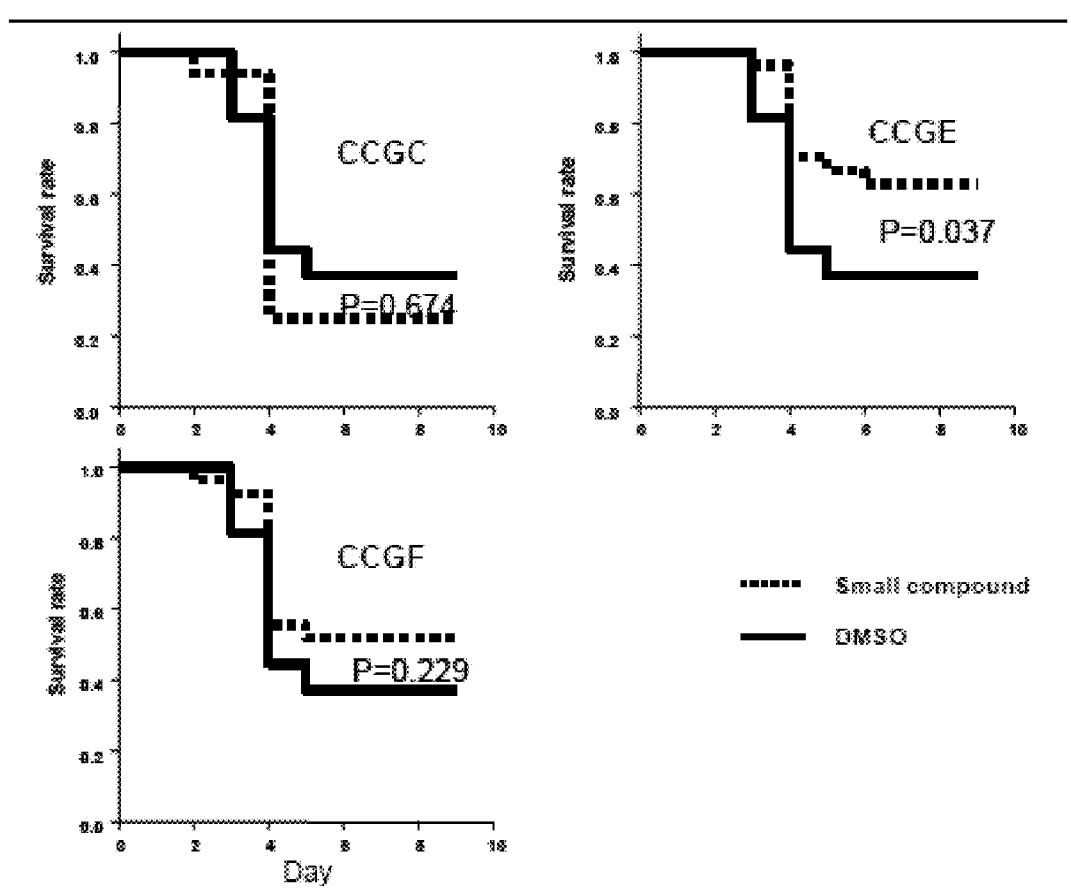
FIG. 13 shows effects of small compounds CCGC (13.8 µM per day), CCGE (12.7 µM per day) and CCGF (14.6 µM per day) on Tg+ mice survival after infected with $6*10^5$ CFU SK(+)GAS. Data were compiled from 4 independent experiments with >16 mice total in each group tested. P values of the difference between control (DMSO) and test group are indicated.
Figure 14:
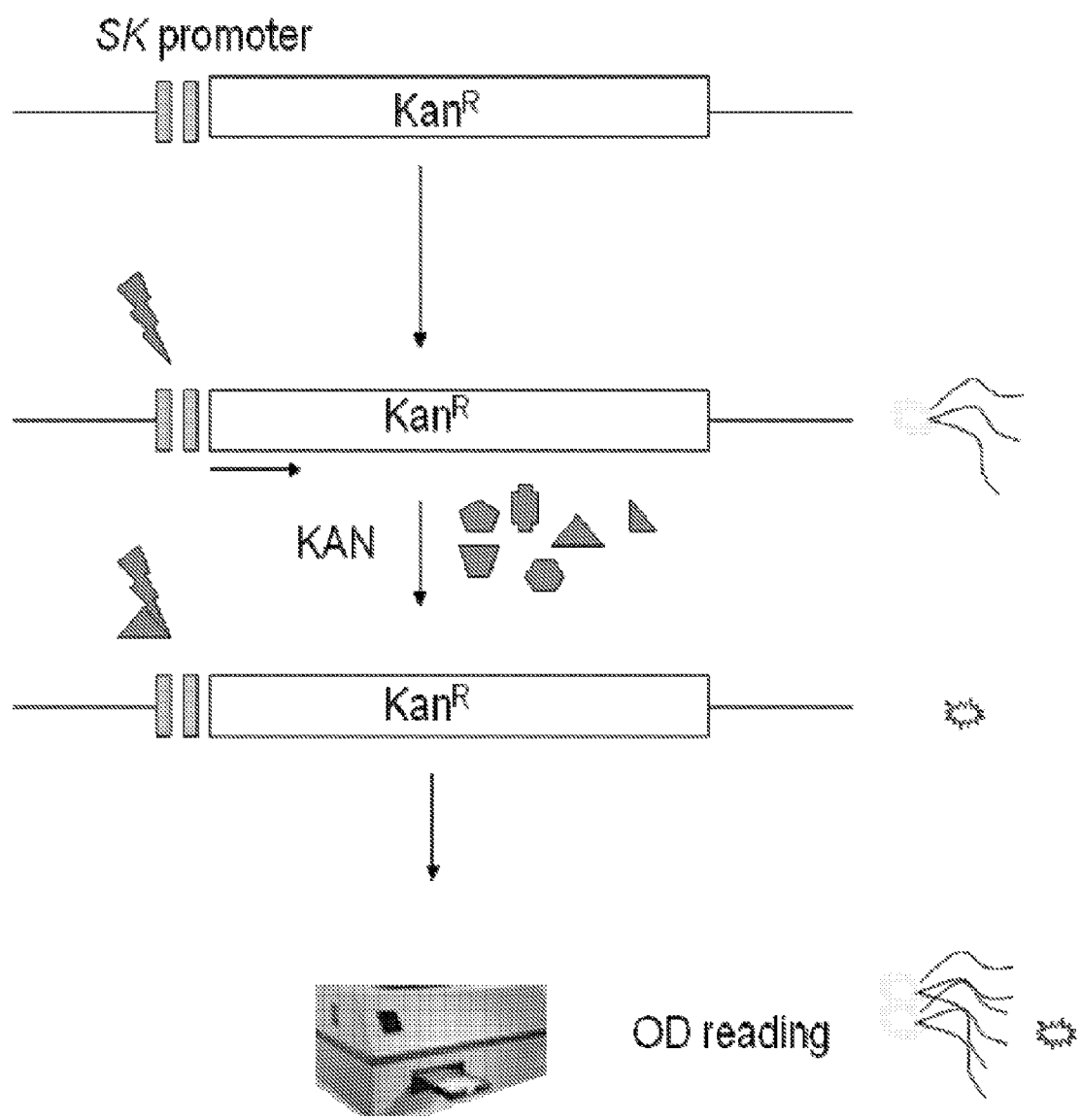
FIG. 14 shows a schematic of a GAS screening assay.
Figure 15:
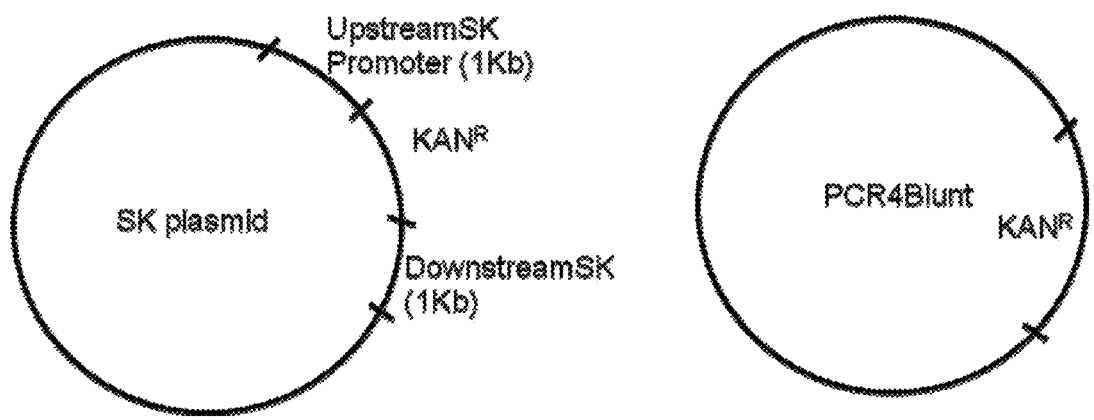
FIG. 15 shows plasmids for use in GAS screening assays.
Figure 16:
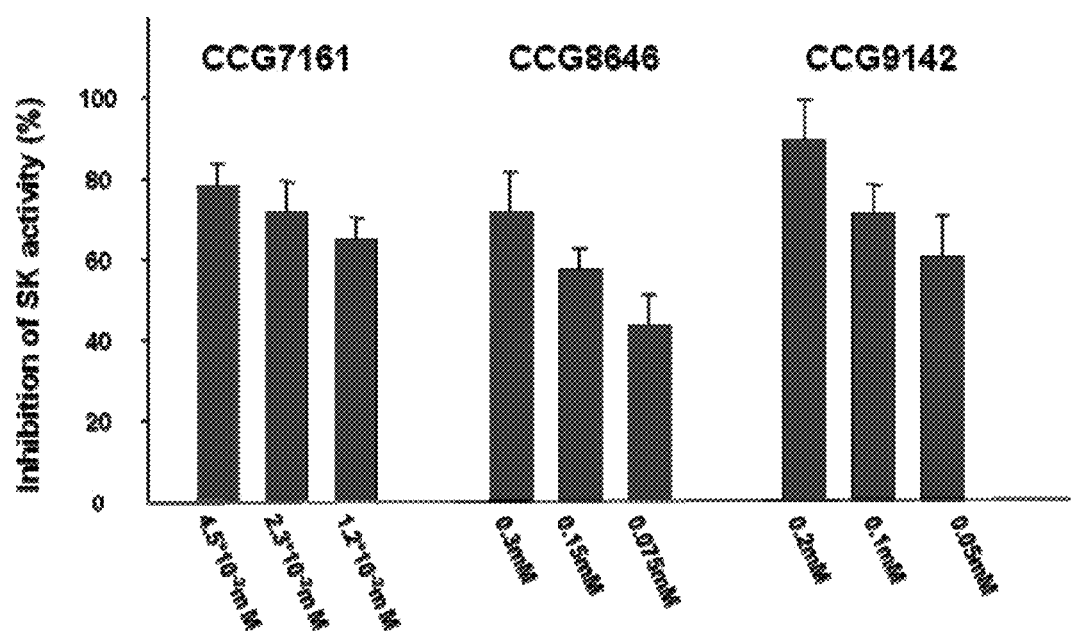
FIG. 16 shows dose response inhibition of SK activity.
Figure 17:
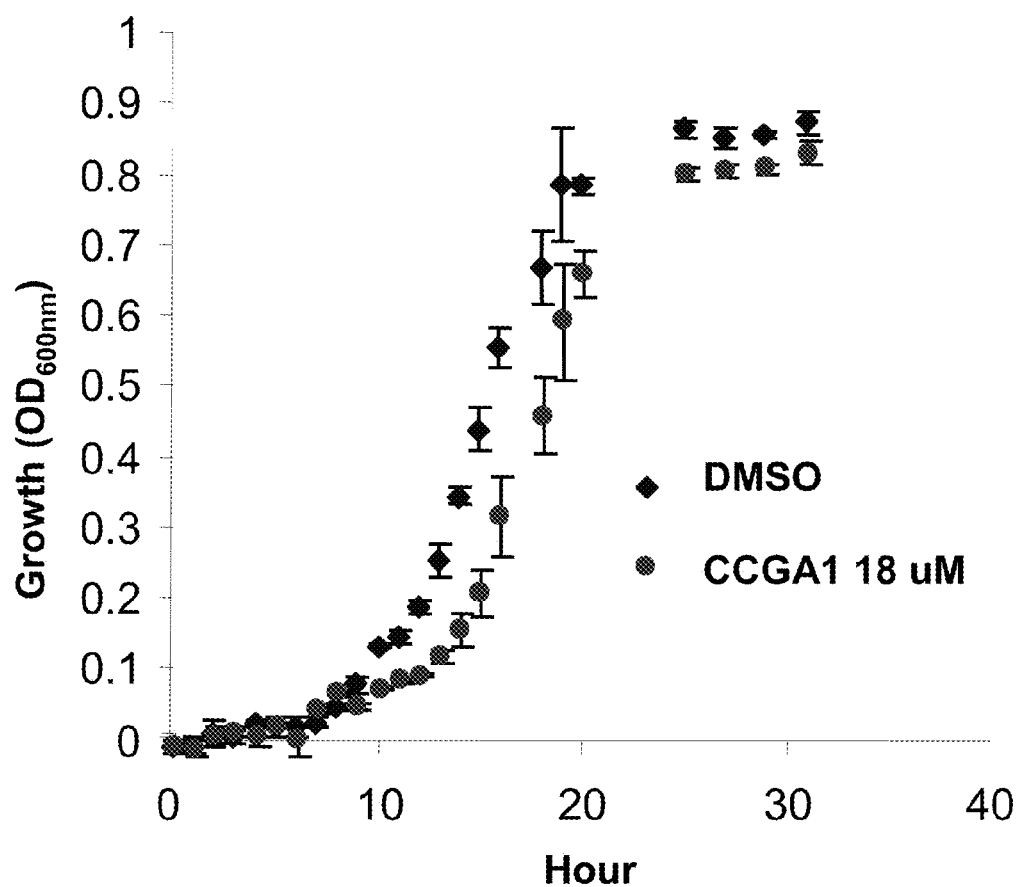
FIG. 17 shows growth of GAS cells in the presence of exemplary inhibitor compounds.
Figure 18:
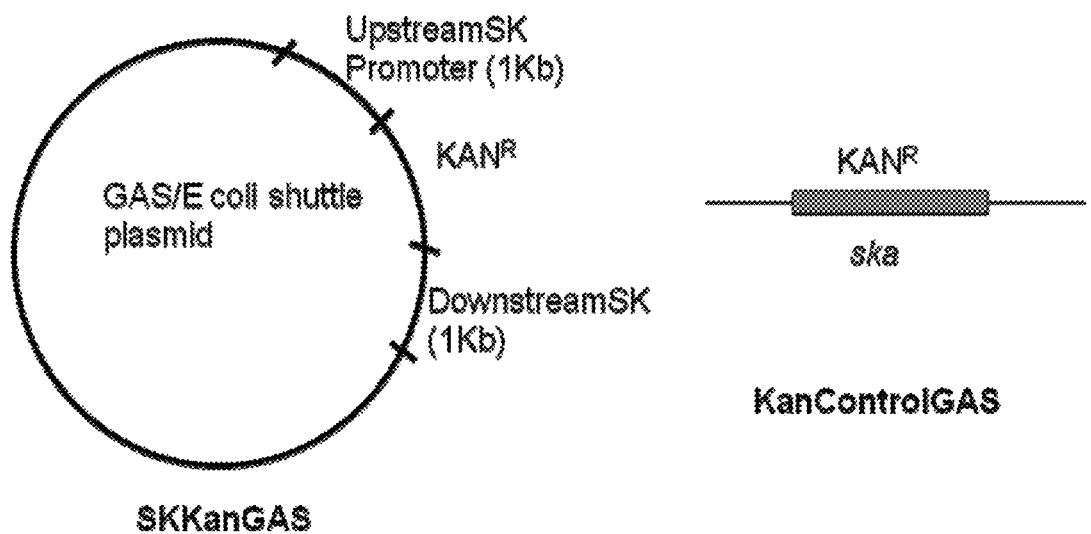
FIG. 18 shows plasmids for use in GAS screening assays.

To examine the in vivo efficacy of compounds CCGC, CCGE, and CCGF, Tg+ mice were first infected with $6*10^5$ CFU SK(+)GAS, then injected with 5 μg of test compound per mouse intraperitoneally daily for 5 days, starting one day after infection. Survival rates are shown in FIG. 13. A significant improvement in survival rate was observed for mice treated with small compound CCGE compared to the DMSO control group (p=0.037). There was also a trend toward improvement in mice treated with small compound CCGF. No improvement was observed in mice treated with small compound CCGC. In some embodiments, small compound are delivered continuously through an ALZET® Osmotic Pump (DURECT Corporation, Cupertino, Calif.).

Example 10

Exemplary Screening Approaches

The NIH Molecular Libraries and Imaging roadmap initiative is used to screen additional compounds. The Molecular Libraries Screening Centers Network (MLSCN), which intends to screen 100-200 HTS assays per year is utilized. The MLSCN is a collaborative research network consisting of 9 extramural centers and 1 NIH intramural screening center and has access to the Small Molecule Repository which maintains a collection of up to 500,000 small compounds.

Assay Implementation.

Only SKKanGAS is used for screening in the primary screening. Briefly, 30 μl THY medium containing 20 μg/ml kanamycin is first plated into 384-well plates (384 microtiter plate, Corning #3701) and compounds are added into the wells. SKKanGAS strain is grown to OD600 nM=0.8. SKKanGAS is then diluted 12.5 fold into 20 μg/ml kanamycin THY medium. SKKanGAS mixture (10 μl) is added into each well of the 384-well plates. The last two columns of the 384-well plate are used as positive control by adding tetracycline (5 μg/ml) which completely inhibits SKKanGAS growth. The plates are cultured at 37° C. for 16-20 hours. Growth of bacteria in each well is measured by absorbance at 600 nm. Z'>0.5, which is compatible with high throughput screening, has been typically obtained with the 384-well plate format in which 55,000 small compounds have been screened. It has also been demonstrated that SKKanGAS growth is not significantly affected by DMSO within concentration from 0.1-1% with the 384-well plate format. SKKanGAS is a BSL2 level agent and can be stored at −80° C. SKKanGAS can be cultured at 37° C. in THY or Bill medium which is commercially available (Fisher Scientific, Pittsburgh, Pa.). Preliminary screening with 2,000 known compounds (The Spectrum Collection, MicroSource Discovery Systems, Inc., Gaylordsville, Conn.) has demonstrated that SKKanGAS growth is susceptible to a number of known antibiotics such as erythromycin and some of its derivatives.

Secondary Screening.

Once hit compounds have been identified by the primary screening, they are applied to dose response assays with both SKKanGAS and SK(−)GAS stains. SKKanGAS and SK(−) GAS are grown in 20 μg/ml kanamycin with serial dilution of hit compounds (DMSO final concentration=1% in THY medium). Plates are incubated at 37° C. for 15-20 hours in a climate controlled room (humidity 50%). The absorbance is measured at 600 nm. pIC50 of growth inhibition of each hit compound is then determined. Compounds that with at least 10 fold lower IC50 in SKKanGAS than SK(−)GAS strain are identified and subjected to secondary confirmatory assay. As a result, dose response assay identifies and eliminates most nonspecific compounds that may inhibit GAS growth or interfere with kanamycin resistance protein function.

The positive compounds identified in dose response assays are subjected to SK assay to identify compounds inhibiting SK expression in SK(+)GAS. Briefly, SK(+)GAS is grown at the presence of hit compounds at a dose range determined by dose response assays within which SK(−) GAS growth is inhibited less than 10% while SKKanGAS growth is inhibited more than 50% under 20 μg/ml kanamycin. After 16-20 hours incubation at 37° C., 25 μl supernatant of SK(+)GAS culture is measured for SK activity using chromogenic substrate 2403 (Diapharma group Inc., West Chester, Ohio) according to the manufacturer's instruction. pIC50 of inhibition of ska expression is estimated.

Optimization Chemistry.

Optimization of the initial hit compounds is supported by the MLSCN to improve their pharmacological properties such as potency and solubility. Initial structure-activity relationship (SAR) is studied and analogues are obtained from a confirmed compound. These analogues are subjected to primary and secondary screening as described above to identify more desirable hit compounds. An optimal compound should have an IC50 in the low μM range or below, good solubility, stability, permeability and low molecular weight allowing room for future chemical engineering. Due to the inherent characteristics of the ska inhibitor screening, only hit compounds with good permeability should be identified.

HTS Informatics.

Informatics support to track compounds, assays, and screening data are Available. Pubchem is used to access information about active compounds. It is expected that the MLSCN screening will generate a number of hit compounds with variety.

Example 11

Effects of Hit Compounds on GAS Gene Expression by Microarray Assay

Previous studies demonstrated that SK was co-regulated with a number of virulence factors during GAS infection (Kreikemeyer et al., Trends Microbiol. 2003; 11:224-232; Graham et al., Proc. Natl. Acad. Sci. U.S.A 2002; 99:13855-13860; Federle et al., J. Bacteriol. 1999; 181:3649-3657; Kreikemeyer et al., Mol. Microbiol. 2001; 39:392-406). The hit compounds likely target some of the transcriptional factors that regulate a network of virulence factors, including SK. As a result, the primary transcriptional regulation machinery can be inferred by the identity of genes whose expressions are affected by hit compounds with SK.

Microarray assay is used to identify genes whose expression are affected by treatment with the hit compound. Briefly, SK(+)GAS are be grown with DMSO and optimal concentration of hit compounds decided in studies described above. Optimal concentration of hit compounds in treating bacteria is defined taking into account of the toxicity to bacteria growth and inhibition of SK expression. An optimal concentration of treatment will cause less than 20% inhibition of bacterial growth while having more than 50% inhibition of SK expression. Bacteria RNA is then isolated and treated with RNase-free DNase. TaqMan PCR is performed to ensure contamination of genomic DNA is absent.

RML GeneChip targets are prepared as follows: control spike transcript mixes are first added to each RNA samples. First strand cDNA is synthesized and purified. cDNA is fragmented by DNase 1 and 3' end-labeled with biotin-ddUTP. These end-labeled cDNA are used to hybridize a customer genechip consisting of 2636 predicted GAS open reading frame probes.

Profiles of the gene transcription affected by hit compounds are compiled and compared with gene transcriptional profile regulated by known TCSs and 'stand-alone' regulators (Kreikemeyer et al., Trends Microbiol. 2003; 11:224-232). There are potential ~100 transcriptional regulators, including the 13 known TCSs. Depending on the results of this study, many new insights of GAS gene regulation involving ska can be gained. It is known that ska is one of the major virulence factors that are co-regulated with a network of genes by the TCSs. Even though CovRS and FasBCAX system have been studied, very little is known about other TCS systems. These compounds may target systems other than CovRS or FasB-CAX The global change of gene expression due to these hit compounds can elucidate unknown gene regulators or networks. Their functions in addition to ska regulation can also be identified by the change of patterns of other genes. The regulators or TCS that affect the expression of ska are then verified by the strategy described for CovRS and FasBCAX system as following.

Example 12

Test Whether the Hit Compounds Target the CovRS or FasBCAX System

Previous studies demonstrated that ska is subjected to control by two two-component sytems CovRS and FasBCAX (Kreikemeyer et al., Trends Microbiol. 2003; 11:224-232; Graham et al., Proc. Natl. Acad. Sci. U.S.A 2002; 99:13855-13860; Federle et al., J. Bacteriol. 1999; 181:3649-3657; Kreikemeyer et al., Mol. Microbiol. 2001; 39:392-406). Components of the CovRS and FasBCAX are likely targets of the hit compounds. The SK(+)GAS stain is a mutant GAS strain where the CovRS system has been inactivated (Khil et al., J. Infect. Dis. 2003; 188:497-505; Heath et al., Infect. Immun. 1999; 67:5298-5305). As a result, hits generated by screening SKKanGAS. strain are only tested for FasBCAX system.

The transcription offasX is dependent on fasBCA operon (Kreikemeyer et al., Mol. Microbiol. 2001; 39:392-406). FasA is the response regulator and is co-transcribed with fasB and C, FasX is the main effector. In order to test whether the hits interact with the FasBCAX system, the effect of hit compounds on transcription offasX and fasBCA operon is evaluated by northern blot transcription analysis as described by Kreikemeyer et al (Kreikemeyer et al., Mol. Microbiol. 2001; 39:392-406). Briefly, SK(+)GAS is cultured for 16-20 hours at 37° C. at the optimal doses of hit compounds as determined by dose response and growth assay as described above. An optimal dose of hit compounds treatment is defined as the concentration at which SK(+)GAS experiences minimal growth inhibition and maximum inhibition of its SK production. A control culture is set up at the same DMSO concentration as the treated culture. RNA is extracted from both cultures with the RNeasy kit (Qiagen, Valencia, Calif.) from late-log-phase GAS. The RNA samples are then treated with DNase and quantified spectrophotometrically. Northern blots with equal loading of RNA from treated sample and DMSO control are hybridized with fasA and X probes (Kreikemeyer et al., Mol. Microbiol. 2001; 39:392-406) to detect the expression offasBCA operon and fasX. The blots are analyzed on a Typhoon 9410 gel and blot imager (Amersham Biosciences, Piscataway, N.J.). Intensities of fasA and X bands are used as measurement of the expression levels.

Real-time RT-PCR analysis is performed to compare the transcription levels of SK(+)GAS treated with hit compound and DMSO as described by Datta et al (Datta et al., Mol. Microbiol. 2005; 56:681-695). Briefly, the RNA samples are converted into cDNA by random hexamers. A conventional PCR is performed with or without reverse transcriptase to confirm the absence of DNA. Gene expression is quantified by the SYBR Green method using iQ5 Real-Time PCR Detection System (Bio-Rad Laboratories, Hercules, Calif.). Housekeeping gene recA is used as control for normalization of intra- and inter-experimental data. If both fasBCA and fasX expression are decreased, it will indicate that the hit compound is targeting the regulation offasBCA operon. If onlyfasXtranscription is decreased, the hit compound could be targeting FasA protein.

Example 13

Determine the Effects of ska Inhibitors on GAS Infection in Human Plasminogen Transgenic Mice The compounds are tested for suppressing GAS virulence in human plasminogen transgenic mice. Once confirmed of their efficacy, they may be used as antimicrobial reagents to further decipher the virulence mechanism of GAS infection.

Evaluate the Efficacy of Compounds in the Human Plasminogen Transgenic Mouse Model.

A murine GAS infectious model is utilized (Sun et al., Science 2004; 305:1283-1286). The human plasminogen transgenic mice are susceptible to GAS infection due to the SK/PLG interaction. This transgenic mouse serves as an appropriate model to test the efficacy of hit compounds in attenuating GAS virulence and mitigate GAS infection. Once the roles and function of compounds in regulating ska expression and other virulence factors are tested, compounds that are potent inhibitors of ska expression are tested in human plaminogen transgenic mice (Tg+).

Briefly, compounds at 0.1 mg, 1 mg, 10 mg and 100 mg/kg body weight are first injected either intraperitoneally or intravenously into wildtype mice (Tg−) to establish the toxicity levels of the compounds. Mortalities are compared to mice injected with DMSO. In order to minimize the number of mice needed, 10 mice are tested for each dose. Depending on the individual compound tested, the dose ranges are selected for further testing. If a compound causes more than 20% mortality in the testing at dose lower than 1 mg/Kg body weight, it will be considered too toxic for the animal experiments and terminated for future testing. The maximum dose to causing less than 20% mortality will be determined, and is tested on more mice. In the next step, 20 mice in each group which is the number of mice needed to detect 20% difference in mortalities with 95% confidence in a log-rank test in each group will be tested. Data are analyzed by the Kaplan—Meier method. Survival in different groups will be compared using the log-rank test.

The concentrations of compounds used to treat mice are adjusted empirically after obtaining the dose ranges of the in vivo toxicity of the compounds. As the effective concentration of compound in vivo is difficult to infer from in vitro data, the experimental dose for in vivo treatment will start at the maximum dose that does not increase mortality of mice more than 20% in the toxicity test, while also taking into account of the availability of the compounds. If the selected concentration of compound is proved effective in protecting animals from GAS infection in the following experiments, the treatment concentration are lowered 10 fold and tested again to reach an optimal concentration. The optimal concentration is defined as the one offering maximum protection of the mice.

Tg+ mice are then used to test the efficacy of compounds in attenuating the virulence of GAS infection. 20 Tg+ mice are infected with $10^5$ CFU of SK(+)GAS then injected with the estimated experimental doses of the compounds two hours later. Survival is monitored for 9 days, while a control group of Tg+ mice will be infected with SK(+)GAS injected with DMSO. The comparison of mortalities between the two groups is analyzed as described above in the toxicity test. Treating mice with compound post-infection helps avoid potential side-effects of toxic or growth inhibition of compound on SK(+)GAS at the time of infection. As a result, the effect of compound on mice survival is a more authentic reflection of the efficacy of compound on inhibiting GAS virulence. Possible scenarios include:

1) Mice treated with compound are less susceptible to SK(+) GAS infection than control treated with DMSO. The compound is then be considered effective in suppressing GAS virulence and be subjected to future studies.

2) Mice treated with compound are as susceptible to SK(+) GAS infection as the control. Then Tg+ mice are injected with compound daily for the duration of the experiment each day. Mortality is monitored and compared to control. If necessary, Tg+ mouse are treated with compound continuously using ALZET® Osmotic Pumps (DURECT Corporation, Cupertino, Calif.). If continuous treatment of compound is necessary to improve Tg+ mice survival, the compound is also considered effective and will be subjected to future studies.

The compound(s) that confer protection against GAS infection in Tg+ mice may be employed in the future study of SK function. In addition, these compounds serve as leads for future optimization of novel antimicrobial reagents.

Example 14

Additional Inhibitors

This Example describes the synthesis and analysis of exemplary GAS inhibitors.

Synthetic Schemes

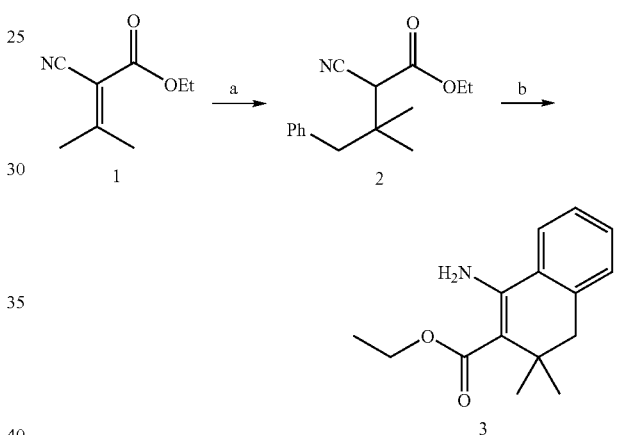

a) BnMgCl, Et$_2$O, 25° C., 3 h; b) conc. H$_2$SO$_4$, 25° C. 24 h

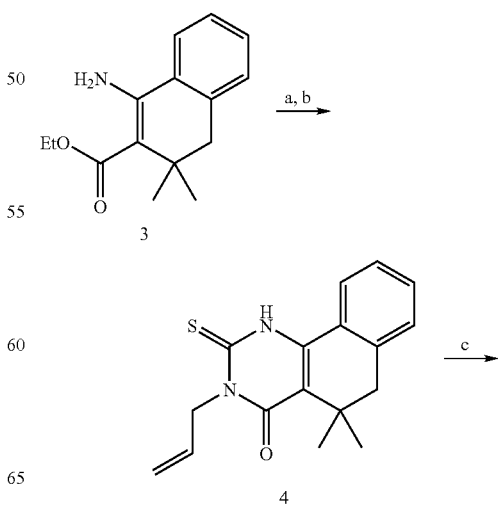

Examples 16-19 a) allylisothiocyanate, EtOH, reflux, 24 h; b) NaOEt, reflux, 48 h; c) KOH, R¹X, EtOH, reflux.

Scheme 3.

Example 14

Example 15 a) MeI, KOH, EtOH, 25° C., 15 min; b) NaOEt/EtOH, 40° C., 48 h.

Scheme 4.

Example 14

Example 20 a) 2.5 eq mCPBA; DCM, RT. b) ethylamine, K$_2$CO$_3$; 1:1 DMF:THF, RT.

Scheme 5.

7

8

9

Example 21 a) 3 eq NaH, DMC; THF, 80 C. 4 hours. b) 45 eq. NH4OAc; MeOH, reflux, 48 hours. c) 4 eq. allyl isothiocyanate; pyridine, reflux, 16 hours. d) 2 eq p-toluenesulfonic acid 2-methoxyethyl ester, Cs$_2$CO$_3$; 2-butanone, reflux, 16 hours.

Scheme 6.

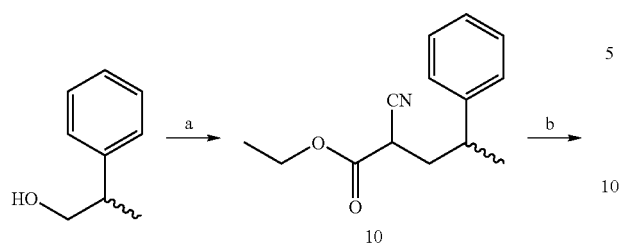

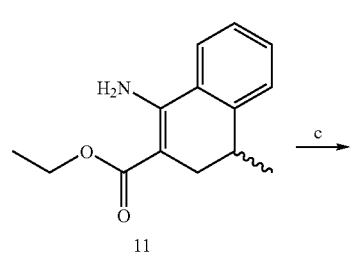

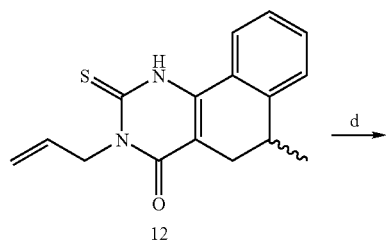

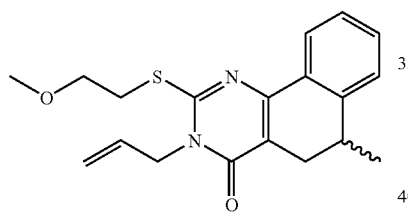

Example 22 a) PPh₃, DIAD, ethyl cyanoacetate; THF, 2 hours at -20 C., then 20 hours at 4 C. b) 4.5 eq TfOH; DCM, 16 hours, RT. c) 4 eq. allyl isothiocyanate, AcOH; EtOH, reflux, 16 hours. d) 2 eq p-toluenesulfonic acid 2-methoxyethyl ester, Cs₂CO₃; 2-butanone, reflux, 16 hours.

Scheme 7.

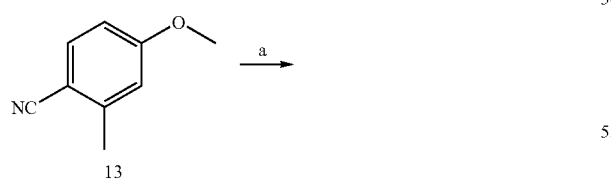

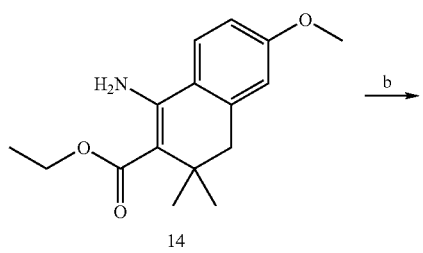

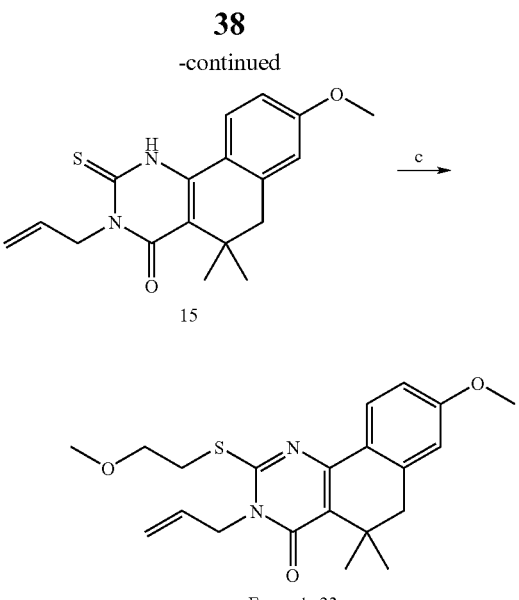

Example 23 a) LDA, ethyl-3,3-dimethylacrylate, ZnI2; diglyme, -78 C.-RT, 3 hours. b) 5 eq allyl isothiocyanate, AcOH; EtOH, reflux, 16 hours. c) 2 eq. p-toluenesulfonic acid 2-methoxyethyl ester, Cs₂CO₃; 2-butanone, 16 hours.

Scheme 8.

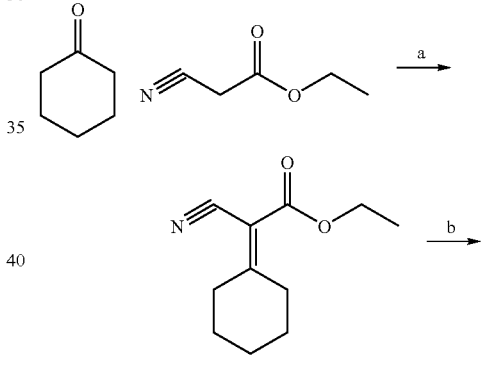

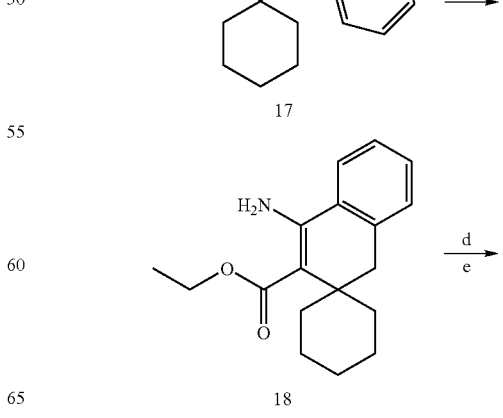

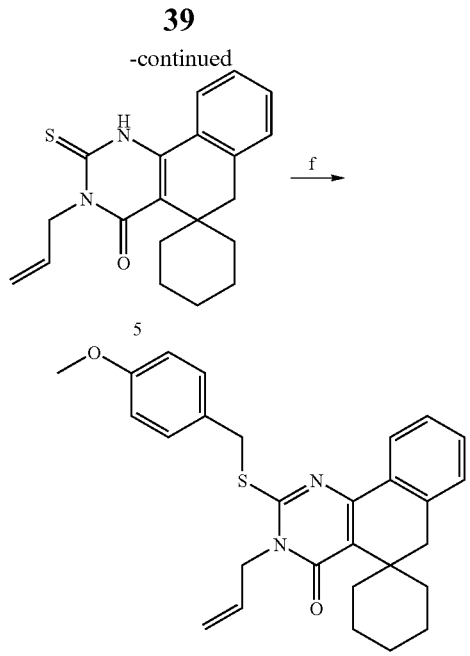

Example 2
(a) NH₄OAc, AcOH, toluene, reflux, 5 h; (b) BnMgCl, Et₂O, rt; (c) H₂SO₄, 0° C. to rt;
(d) allyl isothiocyanate, EtOH, reflux 10 h; (e) KOH, H₂O, reflux, 3 h;
(f) 4-MeO—Ph—CH₂Br, KOH, EtOH, reflux, ON.

Preparations

Preparation of 2 (Scheme 1): Ethyl 2-cyano-3,3-dimethyl-4-phenylbutanoate

To a solution of ethyl 2-cyano-3-methylbut-2-enoate (0.91 mL, 6 mmol) in ether (4 mL) under N₂ was added 1.0 M benzylmagnesium chloride in ether (9 mL, 9 mmol) dropwise to give a pale yellow solution. The reaction was stirred at room temperature for 3 h, and was then cooled to 0° C. and acidified with 10% HCl (10 mL). The organic layer was isolated, washed with water and brine, dried over Na₂SO₄, and concentrated under reduced pressure to give bright yellow oil. Purification by flash column chromatography (10% ethyl acetate in hexanes, $R_f$=0.26) gave the title compound as a pale yellow oil (1.08 g, 73.5%). ¹H NMR (500 MHz, CDCl₃) δ 8.02 (d, J=7.6 Hz, 1H), 7.51 (t, J=7.6 Hz, 1H), 7.32 (t, J=7.6 Hz, 1H), 7.22 (d, J=7.6 Hz, 2H), 4.22 (m, 2H), 3.44 (s, 1H), 3.07 (d, J=16.5 Hz, 1H), 2.83 (d, J=16.5 Hz, 1H), 1.28 (t, J=7.1 Hz, 2H), 1.18 (s, 3H), 1.15 (s, 3H).

Preparation of 3 (Scheme 1): Ethyl 1-amino-3,3-dimethyl-3,4-dihydronaphthalene-2-carboxylate Concentrated H₂SO₄ (2.35 mL, 44.0 mmol) was added dropwise to ethyl 2-cyano-3,3-dimethyl-4-phenylbutanoate (1.08 g, 4.4 mmol) at 0° C. to give an orange solution. The reaction was allowed to warm to room temperature and was stirred for 24 h. Ice water (10 mL) was added to the deep red reaction to give an opaque yellow mixture. The reaction was basified with NH₄OH (20 mL) and extracted with ether (3×10 mL). The organic extracts were washed with water and brine, dried over Na₂SO₄, and concentrated under reduced pressure to give bright yellow oil. Purified by flash column chromatography (20% ethyl acetate in hexanes, $R_f$=0.30) afforded the title compound as bright yellow crystalline solid (392.4 mg, 36.4% yield). ¹H NMR (500 MHz, CDCl₃) δ 7.39 (d, J=7.5 Hz, 1H), 7.31-7.28 (m, 2H), 7.18 (d, J=7.2 Hz, 1H), 6.33 (s, 2H), 4.26 (q, J=7.1 Hz, 2H), 2.65 (s, 2H), 1.34 (t, J=7.1 Hz, 3H), 1.20 (s, 6H).

Preparation of 4 (Scheme 2): 3-Allyl-5,5-dimethyl-2-thioxo-2,3,5,6-tetrahydrobenzo[h]quinazolin-4(1H)-one A solution of ethyl 1-amino-3,3-dimethyl-3,4-dihydronaphthalene-2-carboxylate 3 (Scheme 1, 287.8 mg, 1.2 mmol) and allylisothiocyanate (0.14 mL, 1.4 mmol) was prepared in ethanol (2.0 mL) and was heated at reflux for 24 h. 2 M NaOEt (1.2 mL, 2.4 mmol) was added to the reaction which was then refluxed for an additional 24 h. The reaction was cooled to room temperature, and 10% HCl (1 mL) and water (2 mL) were added. The reaction was extracted with ethyl acetate (3×4 mL), and the combined organic extracts were washed with H₂O, dried over Na₂SO₄. The solvent was evaporated under reduced pressure to give title compound as oily brown solid (153.1 mg, 42.8% crude, over 2 steps). Due to low solubility the material was carried forward without purification. ¹H NMR (500 MHz, CDCl₃) δ 9.30 (s, 1H), 8.02 (d, J=7.6 Hz, 1H), 7.39 (t, J=7.6 Hz, 1H), 7.32 (t, J=7.6 Hz, 1H) 7.22 (d, J=7.6 Hz, 1H), 6.00 (ddt, J=17.2, 10.3, 5.7 Hz, 1H), 5.37 (d, J=17.2 Hz, 1H), 5.27 (d, J=10.3 Hz, 1H), 5.07 (d, J=5.7 Hz, 2H), 2.78 (s, 2H), 1.34 (s, 6H).

Preparation of 5 (Scheme 8). 3-allyl-2-thioxo-2,3-dihydro-1H-spiro[benzo[h]quinazoline-5,1'-cyclohexan]-4(6H)-one Ethyl 4'-amino-1'H-spiro[cyclohexane-1,2'-naphthalene]-3'-carboxylate 18 (Scheme 8, 1.66 g, 5.82 mmol) and allyl isothiocyanate (0.600 ml, 6.13 mmol) were dissolved in Ethanol (9.69 ml) and refluxed at 85° C. for 10 h. A solution of potassium hydroxide (0.653 g, 11.63 mmol) in Water (9.69 ml) was then added and the reaction mixture was refluxed for 3 h. The cooled rxn mixture was acidified to pH 3.0-3.5. The precipitate was filtered off, washed with water and recrystallized from butanol.

Preparation of 6 (Scheme 4): 3-Allyl-2-(methylsulfonyl)-3H-spiro[benzo[h]quinazoline-5,1'-cyclohexan]-4(6H)-one 3-allyl-2-(methylthio)-3H-spiro[benzo[h]quinazoline-5,1'-cyclohexan]-4(6H)-one (Example 14, 450 mg, 1.28 mmol) was dissolved in 19.4 mL of dichloromethane, and 70% mCPBA (787 mg, 3.19 mmol) was then added and the solution allowed to stir for 16 hours at room temperature under nitrogen. At this point the consumption of the starting material was confirmed by thin-layer chromatography, so the reaction mixture was diluted with additional dichloromethane, and then washed sequentially with saturated aqueous sodium bicarbonate solution, water, and brine. The organic layer was partitioned off, dried over MgSO₄, vacuum filtered, and purified in vacuo. The target sulfone compound was isolated by silica flash chromatography (50 g column, 5% ethyl acetate: hexanes) as a white crystalline solid in 62.3% yield (306 mg, 0.796 mmol).

Preparation of 7 (Scheme 5)

An 80% suspension of sodium hydride in mineral oil (280 mg, 9.36 mmol) was added to dry dimethyl carbonate (2.62 mL) at 80° C. 3,3-dimethylindanone (500 mg, 3.12 mmol) was dissolved in dry tetrahydrofuran (4 mL) and then added to the dimethyl carbonate suspension via syringe pump over the course of 1 hour. The reaction mixture was then allowed to stir for an additional 3 hours at 80° C. Thin-layer chromatography after 3 hours confirmed the complete consumption of the starting material, so the reaction was halted by the addition of 10 mL of water. This mixture was then extracted 3× with diethyl ether. The organic layer was washed with H2O and brine, then dried over $MgSO_4$, vacuum filtered, and concentrated in vacuo, leaving a reddish-yellow oil. $^1$H NMR confirms that this is a mixture of p-keto ester 7 and its enol tautomer. Yield=97.5% (664 mg, 3.04 mmol).

Preparation of 8 (Scheme 5)

To a solution of beta-keto ester 7 (664 mg, 3.04 mmol) in methanol (9.2 mL) was added ammonium acetate (5.85 g, 76 mmol). The reaction mixture was tightly capped and warmed to reflux for 18 hours. At this time, additional ammonium acetate (4.68, 60.8 mmol) was added and the reaction recapped and stirred for another 24 hours. The solution was then evaporated to dryness, and the residue redissolved in ethyl acetate and washed sequentially with saturated aqueous sodium bicarbonate, water, and brine. The organic layer was dried over $MgSO_4$, vacuum filtered, and concentrated in vacuo. Purification of the crude material via flash chromatography (50 g silica column, 10% ethyl acetate:hexanes) afforded 365 mg of 8 as a tan solid, yield=55%.

Preparation of 9 (Scheme 5)

Compound 8 (125 mg, 0.575 mmol) was added to a threaded glass vial containing pyridine (0.77 mL). Allyl isothiocyanate (55.6 μL, 0.575 mmol) was added and the reaction vial tightly capped. The solution was warmed to reflux and allowed to stir 1 hour. 3 additional equivalents of allyl isothiocyanate (167 μL in total) were added over the next 3 hours, and the reaction mixture was then allowed to stir at reflux overnight. After 16 hours, the reaction mixture was diluted with $H_2O$ and organics were extracted using ethyl acetate. The combined organic layers were washed with water and brine, then dried over $MgSO_4$, vacuum filtered, and concentrated in vacuo. Silica flash chromatography (10 gram column, 15 ethyl acetate:hexanes) allowed the purification of thiourea compound 9 as a white solid in 28.1% yield (46 mg, 0.162 mmol).

Preparation of 10 (Scheme 6)

To 2.5 mL of dry tetrahydrofuran at −20° C. under nitrogen atmosphere was added triphenylphosphine (577 mg, 2.21 mmol) and diisopropyl azodicarboxylate (444 mg, 2.21 mmol). A light yellow precipitate quickly formed. A solution of commercially available racemic 2-phenyl-1-propanol (200 mg, 1.47 mmol) and ethyl cyanoacetate (500 mg, 4.41 mmol) in 2.5 mL dry tetrahydrofuran was then added to the reaction flask by syringe. Reaction was allowed to stir at −20° C. for 3 hours, then moved to a 4° C. refrigerator for an additional 20 hours. After 20 hours, the THF was removed from the reaction mixture in vacuo and the resulting residue subjected immediately to silica flash chromatography (50 g column, 10% ethyl acetate:hexanes). Target compound was isolated as a light yellow oil in 82.4% yield (280 mg, 1.21 mmol).

Preparation of 11 (Scheme 6)

Cyanoester compound 10 (114 mg, 0.493 mmol) was dissolved in 4.8 mL of dichloromethane. Trifluoromethanesulfonic acid (324 mg, 2.16 mmol) was added to the reaction mixture dropwise and the resulting solution was allowed to stir overnight. Thin-layer chromatography after 16 hours indicated complete consumption of the starting material, so the reaction was quenched by addition of 5 mL saturated aqueous sodium bicarbonate. The organic layer was drained off and the water layer was extracted 3× with ethyl acetate. The organic layers were combined and washed in sequence with water and brine, then dried over $MgSO_4$, vacuum filtered, and concentrated in vacuo. Removal of the solvent leaves 112 mg of yellow crystals found to be unsaturated aminoester intermediate by $^1$H NMR. Yield=98%.

Preparation of 12 (Scheme 6)

To 1.8 mL of absolute ethanol were added aminoester 11 (310 mg, 1.34 mmol), allyl isothiocyanate (268 μL, 2.68 mmol), and acetic acid (161 mg, 2.68 mmol). The reaction vessel was tightly capped and warmed to reflux. The reaction mixture was stirred for 12 hours; an additional 268 μL of allyl isothiocyanate was then added and the mixture stirred for 6 additional hours at reflux. At this point the ethanol was removed in vacuo and the resulting residue was redissolved in ethyl acetate and washed with water and brine. The organic layer was dried over $MgSO_4$, vacuum filtered, and concentrated in vacuo. Silica flash chromatography (100 g column, 5-10% ethyl acetate:hexanes) afforded 135 mg (yield=35.4%) of the desired product as a white powdery solid.

Preparation of 14 (Scheme 7)

Diisopropylamine (775 uL, 5.44 mmol) in diglyme (12.8 mL) was cooled to −78° C. in a dry ice/acetone bath under N2. A 2.5M solution of n-butyllithium (2.2 mL, 5.4 mmol) was then added slowly. The reaction vessel was warmed to 0° C. for 5 minutes then re-cooled to −78° C. Commercially available 4-methoxy-2-methylbenzonitrile 13 was then added dropwise and allowed to stir for 20 minutes. At the same time, 4.8 mL of diglyme was cooled to −78° C. in a separate flask under $N_2$, to which zinc dust (444 mg, 6.79 mmol) was added. Iodine was then added in 2 portions over 10 min, then the mixture was allowed to warm to RT. The mixture was warmed with a heat gun periodically (about 30 seconds every 5 minutes) until all of the iodine appeared consumed and the mixture turned a metallic white-silver. Ethyl 3,3-dimethylacrylate (348 mg, 2.72 mmol) was then added to the first reaction vessel slowly dropwise. Once this addition was complete, the contents of the second flask were poured into the first reaction vessel. The resulting mixture was allowed to warm to room temperature and stir for 2 hours, at which point 25 mL of saturated aqueous ammonium chloride solution was added to halt the reaction. The biphasic solution was loaded into a separatory funnel, and extracted 3× with diethyl ether. The combined organic layers were then washed 3× with water and 1× with brine. After drying the organic layers over $MgSO_4$, vacuum filtering, and concentration in vacuo, the resulting residue was purified via silica flash chromatography (50 g column, 15% ethyl acetate:hexanes). Column purification afforded compound 14 as 323 mg of a yellow crystalline solid, a 43.2% yield.

Preparation of 15 (Scheme 7)

Aminoester compound 14 (263 mg, 0.955 mmol) and acetic acid (109 μL, 1.91 mmol) were added to 1.3 mL of absolute ethanol. Allyl isothiocyanate (186 μL, 1.91 mmol) was then added, and the reaction tightly capped and warmed to reflux. An additional 3 eq of allyl isothiocyanate (279 µL, 2.87 mmol) was added in 3 equal portions over the next 4 hours. Upon completion of all additions, the reaction was allowed to stir for another 12 hours. At this point, the reaction mixture was diluted with water and extracted 3× with ethyl acetate. The organic layer was washed with water and brine, then dried over $MgSO_4$, vacuum filtered, and concentrated in vacuo, leaving a residue of brown oil and white crystals. Silica flash chromatography (25 g column, 10% ethyl acetate: hexanes) isolated 191 mg (0.582 mmol, 60.9% yield) of a granular white solid identified as thiourea compound 15.

Preparation of 16 (Scheme 8). Ethyl 2-cyano-2-cyclohexylideneacetate

To a solution of cyclohexanone (1.50 ml, 14.47 mmol) in toluene (24.12 ml) was added ethyl cyanoacetate (1.556 ml, 14.62 mmol), acetic acid (0.166 ml, 2.89 mmol), and ammonium acetate (0.112 g, 1.447 mmol). The mixture was heated to a reflux at 150° C. in a Dean-Stark apparatus. After 5 h, the reaction was cooled and washed with water and saturated $NaHCO_3$ solution. The organics were dried over $Na_2SO_4$, filtered, and concentrated.

Preparation of 17 (Scheme 8). Ethyl 2-(1-benzylcyclohexyl)-2-cyanoacetate

1 M Benzylmagnesium chloride in diethyl ether (18.92 ml) was added dropwise to ethyl 2-cyano-2-cyclohexylideneacetate (1.828 g, 9.46 mmol) in diethyl ether (6.31 ml) at 23° C. The mixture was stirred at room temperature for 3 days. Then 10% hydrochloric acid (7.83 ml, 255 mmol) was added dropwise at 0° C. while stirring. The organic layer was separated, washed with water, dried over $Na_2SO_4$, filtered, and concentrated.

Preparation of 18 (Scheme 8). Ethyl 4'-amino-1'H-spiro[cyclohexane-1,2-naphthalene]-3'-carboxylate Concentrated $H_2SO_4$ (4.59 ml) was added dropwise to ethyl 2-(1-benzylcyclohexyl)-2-cyanoacetate (2.46 g, 8.62 mmol) at 0° C. The mixture was stirred at room temperature for 7 h. Ice water was added to the mixture resulting in a precipitate. The precipitate was taken up in $Et_2O$ and washed with 28% $NH_3$ solution. The organics were washed with water, dried over $Na_2SO_4$, filtered, and concentrated to an orange oil.

Example Compound 2

3-allyl-2-(4-methoxybenzylthio)-3H-spiro[benzo[h]quinazoline-5,1'-cyclohexan]-4(6H)-one A mixture of 3-allyl-2-thioxo-2,3-dihydro-1H-spiro[benzo[h]quinazoline-5,1'-cyclohexan]-4(6H)-one (5, 0.100 g, 0.295 mmol), paramethoxybenzyl bromide (0.047 ml, 0.325 mmol), potassium hydroxide (0.025 g, 0.443 mmol) in Ethanol (1.738 ml) was refluxed overnight. 1 ml of water was added to the cooled reaction and the mixture was extracted with EtOAc 2×. The combined organics were washed with brine, dried over sodium sulfate, filtered, and concentrated. $^1$H NMR (500 MHz, $CDCl_3$) δ ppm 8.17, 7.39-7.24, 6.88, 5.93, 5.31-5.26, 4.68, 4.57, 3.82, 3.07, 2.61, 1.75-1.72, 1.60-1.53, 1.43-1.37; MS (EI) m/z 459 (M+1)

Example Compound 3

3-allyl-2-(3-methoxybenzylthio)-3H-spiro[benzo[h]quinazoline-5,1'-cyclohexan]-4(6H)-one A mixture of 3-allyl-2-thioxo-2,3-dihydro-1H-spiro[benzo[h]quinazoline-5,1'-cyclohexan]-4(6H)-one (5, 0.075 g, 0.222 mmol), 3-methoxybenzyl bromide (0.034 ml, 0.244 mmol), potassium hydroxide (0.019 g, 0.332 mmol) in Ethanol (1.303 ml) was refluxed overnight. To the cooled solution, water (1 ml) was added and the product was extracted with 10% MeOH in EtOAc, dried over sodium sulfate, and concentrated. The title compound was purified by flash column chromatography, eluting with 0 to 5% EtOAc in hexane. $^1$H NMR (500 MHz, $CDCl_3$) δ ppm 8.15, 7.38-7.23, 7.06-7.02, 6.86-6.84, 5.945.32, 5.32-5.27, 4.69, 4.59, 3.77, 3.06, 2.60, 1.75-1.72, 1.60-1.54, 1.43-1.37; MS (EI) m/z 459 (M+1)

Example Compound 5

3-allyl-2-(4-methoxyphenethylthio)-3H-spiro[benzo[h]quinazoline-5,1'-cyclohexan]-4(6H)-one The title compound was prepared by the same method as described for Example 3 with 4-methoxyphenethyl bromide. $^1$H NMR (500 MHz, $CDCl_3$) δ ppm 8.16, 7.39-7.21, 6.88, 5.96, 5.32-5.28, 4.70, 3.83, 3.52, 3.07, 2.65-2.59, 1.75-1.72, 1.61-1.54, 1.43-1.41; MS (EI) m/z 473 (M+1)

Example Compound 6

N-(4-((3-allyl-4-oxo-4,6-dihydro-3H-spiro[benzo[h]quinazoline-5,1'-cyclohexane]-2-ylthio)methyl)phenyl)acetamide A mixture of 3-allyl-2-thioxo-2,3-dihydro-1H-spiro[benzo[h]quinazoline-5,1'-cyclohexan]-4(6H)-one (5, 0.100 g, 0.295 mmol), 4-acetamidobenzyl chloride (0.060 g, 0.325 mmol), potassium hydroxide (0.025 g, 0.443 mmol), and catalytic sodium iodide (4.43 mg, 0.030 mmol) in ethanol (1.738 ml) was refluxed for 24 h. 1 ml of water was added to the cooled reaction and the mixture was extracted with EtOAc 2×. The combined organics were washed with brine, dried over sodium sulfate, filtered and concentrated. $^1$H NMR (500 MHz, DMSO-$d_6$) δ ppm 9.95, 8.10, 7.51, 7.39-7.32, 5.85, 5.20, 5.13, 4.59-4.56, 3.02, 2.02, 1.70-1.67, 1.60-1.50, 1.28; MS (EI) m/z 486 (M+1)

Example Compound 8

3-allyl-2-(2-methoxyethylthio)-3H-spiro[benzo[h]quinazoline-5,1'-cyclohexan]-4(6H)-one A mixture of 3-allyl-2-thioxo-2,3-dihydro-1H-spiro[benzo[h]quinazoline-5,1'-cyclohexan]-4(6H)-one (5, 0.100 g, 0.295 mmol), 2-Methoxyethyl p-Toluenesulfonate (0.084 ml, 0.325 mmol), potassium hydroxide (0.025 g, 0.443 mmol) in Ethanol (1.738 ml) was refluxed ON. To the cooled solution, water (1 ml) was added and the mixture was extracted with EtOAc 2×. The organics were washed with brine, dried over sodium sulfate, filtered, and concentrated to a yellow oil. The product was purified by flash column chromatography eluting with 0 to 2.5% EtOAc in hexane. $^1$H NMR (500 MHz, $CDCl_3$) δ ppm 8.08, 7.39-7.23, 5.95, 5.33-5.28, 4.71, 3.79, 3.57, 3.45, 3.06, 2.61, 1.75-1.72, 1.60-1.54, 1.42-1.39; MS (EI) m/z 397 (M+1)

Example Compound 9

3-allyl-2-(2-(dimethylamino)ethylthio)-3H-spiro[benzo[h]quinazoline-5,1'-cyclohexan]-4(6H)-one A mixture of 3-allyl-2-thioxo-2,3-dihydro-1H-spiro[benzo[h]quinazoline-5,1'-cyclohexan]-4(6H)-one (5, 0.100 g, 0.295 mmol), beta-dimethylaminoethyl bromide hydrobromide (0.076 g, 0.325 mmol), potassium hydroxide (0.041 g, 0.739 mmol) in Ethanol (1.738 ml) was refluxed ON. To the cooled solution, water (1 ml) was added and the mixture was extracted with EtOAc 2×. The organics were washed with brine, dried over sodium sulfate, filtered, and concentrated. $^1$H NMR (500 MHz, DMSO-$d_6$) δ ppm 8.12, 7.37-7.22, 5.95, 4.71, 3.48, 3.05, 2.76, 2.64-2.58, 2.36, 1.74-1.72, 1.59-1.53, 1.42-1.39; MS (EI) m/z 410 (M+1).

Preparation of 3-Allyl-2-(methylthio)-3H-spiro[benzo[h]quinazoline-5,1'-cyclohexan]-4(6H)-one (Scheme 3)

A solution of 5 (Scheme 8, 75.0 mg, 0.22 mmol) and KOH (1.9 mg, 0.33 mmol) was prepared in ethanol (1.3 mL). Iodomethane (0.021 mL, 0.33 mmol) was added and the reaction was stirred for 15 min at room temperature. Water (7 mL) was added and the reaction was extracted with 10% methanol in ethyl acetate (3×10 mL). The combined organic extracts were dried over MgSO$_4$ and concentrated under reduced pressure to provide title compound as yellow crystalline solid (74.4 mg, 95.0%). $^1$H NMR (500 MHz, DMSO-$d_6$) δ 8.10 (d, J=7.3 Hz, 1H), 7.41-7.33 (m, 3H), 5.88 (ddt, J=17.3, 10.4, 5.3 Hz, 1H), 5.22 (d, J=10.4 Hz, 1H), 5.15 (d, J=17.3 Hz, 1H), 4.60 (d, J=5.3 Hz, 2H), 3.02 (s, 2H), 2.66 (s, 3H), 2.50-2.45 (m, 1H), 1.70-1.67 (m, 1H), 1.57-1.47 (m, H), 1.28-1.17 (M, 3H). ESI+ MS m/z 353.2 (M+1), 375.2 (M+23).

Example Compound 15

3-Allyl-2-ethoxy-3H-spiro[benzo[h]quinazoline-5,1'-cyclohexan]-4(6H)-one

A solution of 3-allyl-2-(methylthio)-3H-spiro[benzo[h]quinazoline-5,1'-cyclohexan]-4(6H)-one (91.0 mg, 0.26 mmol) in 2.0 M sodium ethoxide in ethanol (2.0 mL, 4.0 mmol) was prepared under N$_2$ and heated at 40° C. for 14 h. The reaction was cooled to room temperature, water (7 mL) was added, and the reaction was extracted with ethyl acetate (3×7 mL). The combined organic extracts were washed with brine, dried over MgSO$_4$, and concentrated under reduced pressure to give brown oil. The oil was purified by flash column chromatography (10% ethyl acetate in hexanes, R$_f$=0.36) to afford title compound as white crystalline solid (72.4 mg, 79.5%).

$^1$H NMR (500 MHz, DMSO-$d_6$) δ 8.02 (d, J=7.7 Hz, 1H), 7.39-7.31 (m, 3H), 5.89 (ddt, J=17.2, 10.3, 4.3 Hz, 1H), 5.16 (dd, J=10.3, 1.3 Hz, 1H), 5.09 (dd, J=17.2, 1.3 Hz, 1H), 4.53 (q, J=7.1 Hz, 2H), 4.51 (d, J=4.3 Hz, 2H), 3.00 (s, 2H), 2.50-2.45 (m, 1H), 1.69-1.66 (m, 1H), 1.59-1.46 (m, 5H), 1.37 (t, J=7.1, 3H), 1.25-1.16 (m, 3H).

General Preparation of 3-Allyl-2-(alkylthio)-5,5-dimethyl-5,6-dihydrobenzo[h]quinazolin-4(3H)-ones (Scheme 2, Examples 16-19)

A solution of 3-Allyl-5,5-dimethyl-2-thioxo-2,3,5,6-tetrahydrobenzo[h]quinazolin-4(1H)-one (4, 1.0 equiv) and potassium hydroxide (1.5 equiv) was prepared in ethanol to a final concentration of approximately 0.2 M. The appropriate alkyl halide (1.1 equiv) was added and the reaction was heated at reflux until the starting material was no longer present by TLC. The reaction was cooled to room temperature, water was added, and the reaction was extracted with ethyl acetate. The combined organic extracts were washed with brine, dried over Na$_2$SO$_4$, and concentrated under reduced pressure to give analogues. Analogues were purified by flash column chromatography.

Example Compound 16

3-Allyl-2-(2-methoxyethylthio)-5,5-dimethyl-5,6-dihydrobenzo[h]quinazolin-4(3H)-one Pale yellow crystalline solid (15.8%). R$_f$=0.31, 20% ethyl acetate in hexanes. $^1$H NMR (500 MHz, CDCl$_3$) δ 8.07 (d, J=7.5 Hz, 1H), 7.35 (t, J=7.1 Hz, 1H), 7.31 (t, J=7.1 Hz, 1H), 7.19 (d, J=7.1 Hz, 1H), 5.94 (ddt, J=17.2, 10.3, 5.5 Hz, 1H), 5.29 (d, J=17.2 Hz, 1H), 5.27 (d, J=10.3 Hz, 1H), 4.70 (d, J=5.5 Hz, 2H), 3.77 (t, J=6.2 Hz, 2H), 3.54 (t, J=6.2 Hz, 2H), 3.42 (s, 3H), 2.79 (s, 2H), 1.38 (s, 6H).

Example Compound 17

2-(3-Allyl-5,5-dimethyl-4-oxo-3,4,5,6-tetrahydrobenzo[h]quinazolin-2-ylthio)acetamide White crystalline solid (14.1%). R$_f$=0.22, 80% ethyl acetate in hexanes. $^1$H NMR (500 MHz, CDCl$_3$) δ 8.07 (d, J=7.4 Hz, 1H), 7.35 (p, J=7.4 Hz, 2H), 7.20 (d, J=7.0 Hz, 1H), 6.83 (s, 1H), 5.92 (ddt, J=16.6, 11.0, 5.2 Hz, 1H), 5.59 (s, 1H), 5.30 (d, J=11.0, 1H), 5.30 (d, J=16.6 Hz, 1H), 4.70 (d, J=5.2 Hz, 2H), 3.96 (s, 2H), 2.79 (s, 2H), 1.38 (s, 6H).

Example Compound 18

3-Allyl-5,5-dimethyl-2-(pyridin-2-ylmethylthio)-5,6-dihydrobenzo[h]quinazolin-4(3H)-one Yellow oil (10.3 mg, 17.6%). R$_f$=0.18, 25% ethyl acetate in hexanes. $^1$HNMR (500 MHz, CDCl$_3$) δ 8.60 (d, J=4.2 Hz, 1H), 8.08 (dd, J=7.7, 1.0 Hz, 1H), 7.63 (td, J=7.7, 1.8 Hz, 1H), 7.49 (d, J=7.7 Hz, 1H), 7.35 (dt, J=7.3, 1.4 Hz, 1H), 7.30 (dt, J=7.3, 1.4 Hz, 1H), 7.20 (d, J=7.7 Hz, 1H), 7.19 (t, J=6.3 Hz, 1H), 5.93 (ddt, J=15.7, 9.0, 5.6 Hz, 1H), 5.29 (dd, J=15.7, 1.1 Hz, 1H), 5.26 (dd, J=9.0, 1.1 Hz, 1H), 4.73 (s, 2H), 4.71 (d, J=5.6 Hz, 2H), 2.78 (s, 2H), 1.38 (s, 6H).

Example Compound 19

3-Allyl-2-(2-hydroxyethylthio)-5,5-dimethyl-5,6-dihydrobenzo[h]quinazolin-4(3H)-one Yellow crystalline solid (10.6 mg, 19.3%). R$_f$=0.14, 25% ethyl acetate in hexanes. $^1$H NMR (500 MHz, CDCl$_3$) δ 8.03 (dd, J=7.3, 1.7 Hz, 1H), 7.36 (td, J=7.3, 1.6 Hz, 1H), 7.32 (td, J=7.3, 1.6 Hz, 1H), 7.19 (d, J=7.3 Hz, 1H), 5.93 (ddt, J=18.4, 9.6, 5.6 Hz, 1H), 5.30 (d, J=18.4 Hz, 1H), 5.29 (d, J=9.6 Hz, 1H), 4.72 (d, J=5.6 Hz, 2H), 4.04 (q, J=5.5 Hz, 2H), 3.55 (t, J=5.5 Hz, 2H), 2.89 (t, J=5.5 Hz, 1H), 2.79 (s, 2H), 1.38 (s, 6H).

Example Compound 20

(3-allyl-2-(ethylamino)-3H-spiro[benzo[h]quinazoline-5,1'-cyclohexan]-4(6H)-one)

3-Allyl-2-(methylsulfonyl)-3H-spiro[benzo[h]quinazoline-5,1'-cyclohexan]-4(6H)-one (6, 306 mg, 0.796 mmol) and potassium carbonate (165 mg, 1.19 mmol) were added to 1 mL of dry dimethylformamide stirring under nitrogen atmosphere. A 2.0M solution of ethylamine in tetrahydrofuran (1 mL, 2 mmol) was then added, and the reaction was tightly capped and allowed to stir at room temperature for 5 hours. Another 1 mL portion of ethylamine solution was added at 5 hours, and the reaction allowed to stir for another 12 hours. At this point, the reaction mixture was diluted with diethyl ether and washed twice with water and once with brine. The organic layer was dried over MgSO$_4$, vacuum filtered, and concentrated in vacuo. The residue was then loaded onto a silica flash column (50 g column, 10% to 33% ethyl acetate:hexanes), which isolated title compound in 85% yield (237 mg, 0.678 mmol) as a white crystalline solid. $^1$H NMR (500 MHz, CDCl$_3$) δ ppm: 8.15, 7.33, 7.22, 5.94, 5.35, 5.31, 3.60, 3.04, 2.61, 1.72, 1.58, 1.39, 1.30.

Example Compound 21

(3-allyl-2-(2-methoxyethylthio)-5,5-dimethyl-3H-indeno[1,2-d]pyrimidin-4(5H)-one)

Thiourea compound 9 (37 mg, 0.130 mmol) and cesium carbonate (63.5 mg, 0.195 mmol) were added to 0.75 mL of 2-butanone in a threaded vial. P-toluenesulfonic acid 2-methoxyethyl ester (60 mg, 0.260 mmol) was added, and then the vial was capped tightly and stirred at reflux for 16 hours. At this time, the reaction mixture was evaporated to dryness, and the resultant residue dissolved in ethyl acetate. The organic layer was washed with saturated aqueous ammonium chloride, water, and brine, then dried over MgSO$_4$ and vacuum filtered. The dry organic layer was then concentrated in vacuo; silica flash chromatography isolated the desired methoxyethyl-substituted product as a brown oil, 27.5 mg (61.8% yield). $^1$H NMR (500 MHz, CDCl$_3$) δ ppm: 7.85, 7.49, 7.42, 5.98, 5.33, 5.30, 4.80, 3.80, 3.60, 3.47, 2.20, 1.57.

Example Compound 22

(3-allyl-2-(2-methoxyethylthio)-6-methyl-5,6-dihydrobenzo[h]quinazolin-4(3H)-one)

The title compound was prepared as described for Example 21 using thiourea intermediate 12 (Scheme 6) and p-toluenesulfonic acid 2-methoxyethyl ester in 64.0% yield. $^1$H NMR (500 MHz, CDCl$_3$) δ ppm: 8.15, 7.41, 7.35, 7.31, 5.95, 5.34, 5.30, 4.77, 3.80, 3.58, 3.46, 3.11, 2.92, 2.73, 1.29.

Example Compound 23

(3-allyl-8-methoxy-2-(2-methoxyethylthio)-5,5-dimethyl-5,6-dihydrobenzo[h]quinazolin-4(3H)-one)

The title compound was prepared as in Example 21 from thiourea 15 (Scheme 7) and p-toluenesulfonic acid 2-methoxyethyl ester in 73% yield: NMR (500 MHz, CDCl$_3$) 5 ppm: 8.03, 6.85, 6.73, 5.95, 5.31, 5.28, 4.71, 3.88, 3.77, 3.54, 3.44, 2.77, 1.40.

Tables 2-4 show structures and inhibition data for the above described compounds.

TABLE 2

| CCG/Catalog number | Structure | Example Compound Number |
| --- | --- | --- |
| 575096 (CCG-2979) | 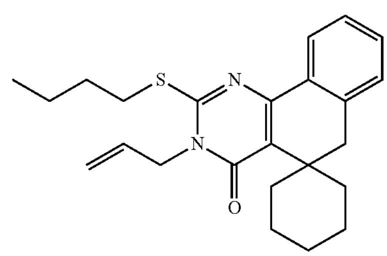 [SMILES: C=CCn1c(SCCCC)nc2c(c1=O)C1(CCCCC1)Cc1ccccc1-2] | 1 |
| CCG-102483 | 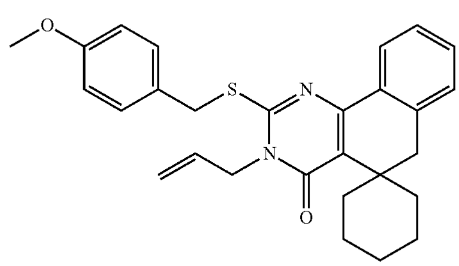 [SMILES: C=CCn1c(SCc2ccc(OC)cc2)nc2c(c1=O)C1(CCCCC1)Cc1ccccc1-2] | 2 |

TABLE 2-continued
| CCG/Catalog number | Structure | Example Compound Number |
|---|---|---|
| CCG-102485 | 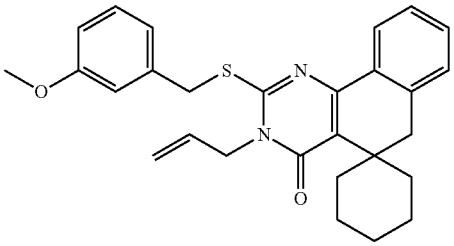 [SMILES: C=CCn1c(SCc2cccc(OC)c2)nc2c(c1=O)C1(CCCCC1)Cc1ccccc1-2] | 3 |
| 575097 (CCG 102487) | 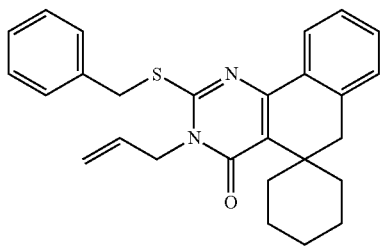 [SMILES: C=CCn1c(SCc2ccccc2)nc2c(c1=O)C1(CCCCC1)Cc1ccccc1-2] | 4 |
| CCG-102489 | 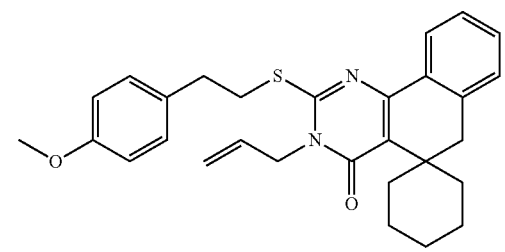 [SMILES: C=CCn1c(SCCc2ccc(OC)cc2)nc2c(c1=O)C1(CCCCC1)Cc1ccccc1-2] | 5 |
| CCG-102491 | 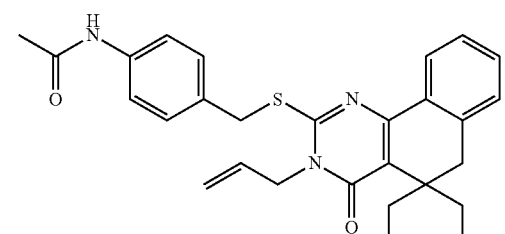 | 6 |
| 25203 | 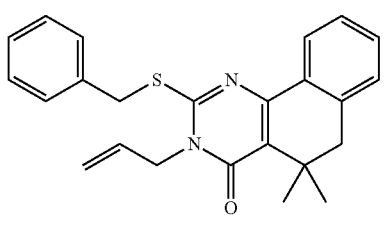 [SMILES: C=CCn1c(SCc2ccccc2)nc2c(c1=O)C(C)(C)Cc1ccccc1-2] | 7 |
| CCG-102493 | 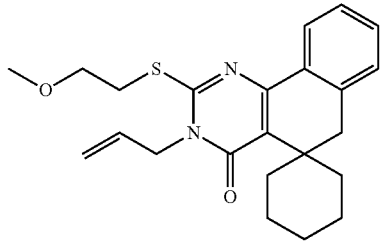 [SMILES: C=CCn1c(SCCOC)nc2c(c1=O)C1(CCCCC1)Cc1ccccc1-2] | 8 |

TABLE 2-continued

| CCG/Catalog number | Structure | Example Compound Number |
|---|---|---|
| CCG-102495 | 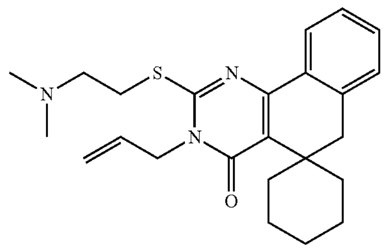 [SMILES: C=CCn1c(SCCN(C)C)nc2c(c1=O)C1(CCCCC1)Cc1ccccc1-2] | 9 |
| AK968 | 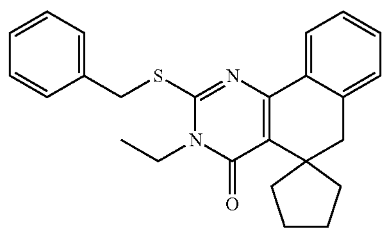 [SMILES: CCn1c(SCc2ccccc2)nc2c(c1=O)C1(CCCC1)Cc1ccccc1-2] | 10 |
| 1S-22207 | 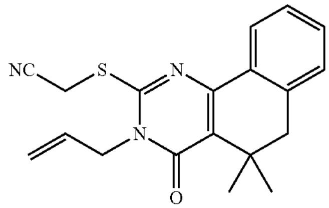 [SMILES: C=CCn1c(SCC#N)nc2c(c1=O)C(C)(C)Cc1ccccc1-2] | 11 |
| 1S-26137 | 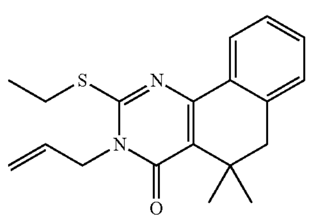 [SMILES: C=CCn1c(SCC)nc2c(c1=O)C(C)(C)Cc1ccccc1-2] | 12 |
| 1S-30398 | 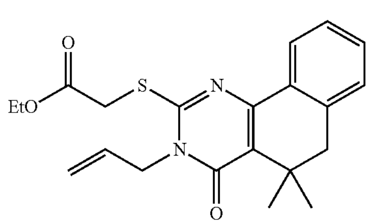 [SMILES: C=CCn1c(SCC(=O)OCC)nc2c(c1=O)C(C)(C)Cc1ccccc1-2] | 13 |
| CCG-102620 | 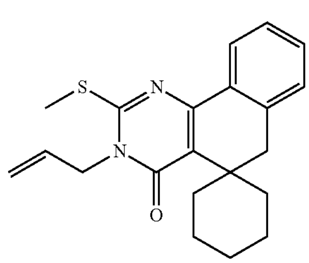 [SMILES: C=CCn1c(SC)nc2c(c1=O)C1(CCCCC1)Cc1ccccc1-2] | 14 |

TABLE 2-continued

| CCG/Catalog number | Structure | Example Compound Number |
|---|---|---|
| CCG-102622 | 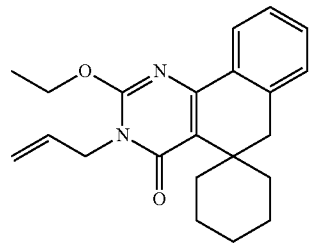 [SMILES: C=CCn1c(OCC)nc2c(c1=O)C1(CCCCC1)Cc1ccccc1-2] | 15 |
| CCG-102624 | 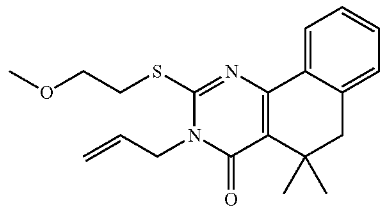 [SMILES: C=CCn1c(SCCOC)nc2c(c1=O)C(C)(C)Cc1ccccc1-2] | 16 |
| CCG-203037 | 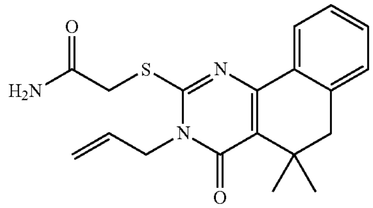 [SMILES: C=CCn1c(SCC(N)=O)nc2c(c1=O)C(C)(C)Cc1ccccc1-2] | 17 |
| CCG-203039 | 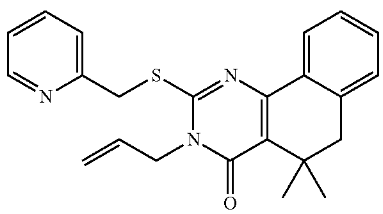 [SMILES: C=CCn1c(SCc2ccccn2)nc2c(c1=O)C(C)(C)Cc1ccccc1-2] | 18 |
| CCG-203041 | 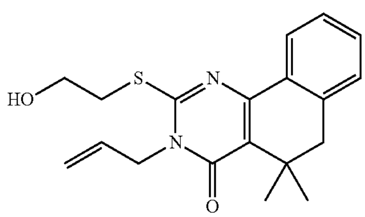 [SMILES: C=CCn1c(SCCO)nc2c(c1=O)C(C)(C)Cc1ccccc1-2] | 19 |
| CCG-203043 | 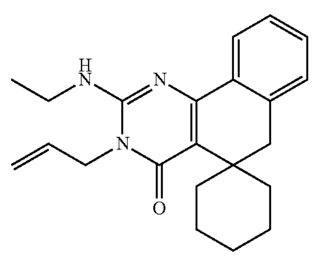 [SMILES: C=CCn1c(NCC)nc2c(c1=O)C1(CCCCC1)Cc1ccccc1-2] | 20 |
| CCG-203572 | 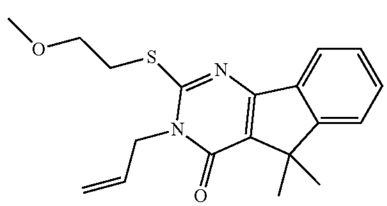 [SMILES: C=CCn1c(SCCOC)nc2c(c1=O)C(C)(C)c1ccccc1-2] | 21 |

TABLE 2-continued

| CCG/Catalog number | Structure | Example Compound Number |
|---|---|---|
| CCG-203574 | (structure) | 22 |
| CCG-203576 | (structure) | 23 |

TABLE 3

| | SK Expression (% control) (compound conc. in µg/ml) | | | | | | | | | | | | |
|---|---|---|---|---|---|---|---|---|---|---|---|---|---|
| CCG\Catalog # | 0.3 | 0.1 | 0.5 | 1.0 | 2.5 | 3 | 5 | 10 | 20 | 30 | 40 | 50 | 60 | 70 |
| 575096 (CCG-2979) | | | | | | | | 105 | 90 | 80 | 68 | 65 | 37 | 40 |
| 575096 (trial 2) | | | | | | | 50 | 38 | 38 | | 51 | | | |
| 575096 (trial 3) | | | | | | | | 104 | 91 | 79 | 69 | 66 | 37 | 40 |
| 575096 (trial 4) | | | | | | | | 79 | 79 | 79 | 76 | 83 | 69 | 61 |
| 575096 (trial 6) | 127 | 95 | | 84 | | 69 | | 47 | | 42 | | | 47 | |
| 575096 (trial 7) | 108 | 77 | | 65 | | 61 | | 57 | | 68 | | | 37 | |
| 575096 (trial 8) | 95 | 83 | | 69 | | 62 | | 58 | | 61 | | | 34 | |
| CCG-102483 | | | | | | | 119 | | | 80 | | | | |
| CCG-102485 | | | | | | | 81 | | | 91 | | | | |
| 575097 (CCG 102487) | | | | | | | | 92 | 82 | 79 | 72 | 70 | 63 | 65 |
| 575097 (trial 2) | | | | | | | | 88 | 79 | 77 | 74 | 67 | | |
| CCG-102489 | | | | | | 91 | | | | 79 | | | | |
| CCG-102491 | | | | | | 85 | | | | 96 | | | | |
| 25203 | | | | 110 | | | | 96 | 84 | 70 | 63 | 58 | 52 | 60 |
| CCG-102493 | | | | 101 | | | 98 | 92 | 100 | 64 | 68 | 49 | 52 | 52 |
| CCG-102493 (trial 2) | | | | | | | | 103 | | | | | | |
| CCG-102493 (trial 2) | | | | | | | 50 | 45 | 39 | | 29 | | | |
| CCG-102493 (trial 3) | 98 | 75 | | 54 | | 51 | | 46 | | 42 | | | 27 | |
| CCG-102495 | | | | | | | | 17 | | | | | | |
| AK968 | | | | | | | | 83 | 64 | 57 | 54 | 40 | 33 | 45 |
| 1S-22207 | | | | | | | 64 | 39 | 31 | 22 | | | | |
| 1S-22207 (trial 2) | | | | | | | 49 | 38 | 27 | 25 | | | | |
| 1S-22207 (trial 3) | 103 | 103 | 102 | 62 | | | | 39 | | 13 | | | 7 | |
| 1S-22207(trial 4) | 104 | 108 | 108 | 46 | | | | 29 | | 8 | | | 4 | |
| 1S-22207 (trial 5) | 95 | 97 | 99 | 83 | | | | 33 | | 11 | | | 6 | |
| 1S-22207 (trial 6) | 108 | 95 | 77 | 47 | | | | 34 | | 21 | | | 27 | |
| 1S-22207 (trial 7) | | | | | | | 80 | | | 40 | | | | |
| 1S-26137 | | | | | | | 21 | 20 | 22 | 19 | | | | |
| 1S-30398 | | | | | | | 42 | 36 | 38 | 39 | | | | |
| CCG-102620 | | | | | | | 62 | 50 | 33 | 27 | | | | |
| CCG-102622 | | | | | | | 43 | 41 | 38 | 23 | | | | |
| CCG-102624 | | | | | | | 30 | 33 | 30 | 23 | | | | |
| CCG-102624 (trial 2) | 97 | 90 | | 79 | | 35 | | 29 | | 26 | | | 28 | |
| CCG-203037 | 97 | 96 | | 96 | | 94 | | 92 | | 79 | | | 38 | |
| CCG-203039 | 95 | 94 | | 93 | | 58 | | 49 | | 35 | | | 27 | |
| CCG-203041 | 90 | 93 | | 90 | | 87 | | 57 | | 28 | | | 12 | |
| CCG-203043 | 96 | 96 | | 94 | | 62 | | 41 | | 32 | | | 24 | |
| CCG-203572 | | | | | | | 21 | 20 | 10 | 9 | | | | |
| CCG-203572 (repeat) | 101 | 100 | | 102 | | 102 | | 51 | | 24 | | | 29 | |
| CCG-203572 (trial 3) | 129 | 128 | | 134 | | 75 | | 12 | | 2 | | | 1 | |
| CCG-203574 | | | | | | | 80 | 10 | 6 | 6 | | | | |
| CCG-203576 | | | | | | | 30 | 27 | 19 | 11 | | | | |
| CCG-203576 (trial 2) | 99 | 99 | | 99 | | 100 | | 88 | | 82 | | | 32 | |
| CCG-203576 (trial 3) | 98 | 93 | | 89 | | 61 | | 49 | | 27 | | | 7 | |

TABLE 4

| CCG\Catalog # | \multicolumn{13}{c}{GAS Growth (% control) (compound conc. in µg/ml)} | | | | | | | | | | | | |
|---|---|---|---|---|---|---|---|---|---|---|---|---|---|
| | 0.1 | 0.3 | 1 | 2.5 | 3 | 5 | 10 | 20 | 30 | 40 | 50 | 60 | 70 |
| 575096 (CCG-2979) | | | | | | | 92 | 84 | 79 | 72 | 73 | 53 | 52 |
| 575096 (trial 2) | | | | | | 101 | 97 | 103 | | 111 | | | |
| 575096 (trial 3) | | | | | | | 88 | 93 | 97 | 100 | 103 | 105 | 115 |
| 575096 (trial 4) | | | | | | | 88 | 89 | 90 | 92 | 93 | 96 | 99 |
| 575096 (trial 6) | 96 | 99 | 98 | | 98 | | 98 | | 98 | | | 99 | |
| 575096 (trial 7) | 97 | 102 | 102 | | 100 | | 102 | | 104 | | | 110 | |
| 575096 (trial 8) | 100 | 99 | 102 | | 102 | | 103 | | 102 | | | 112 | |
| CCG-102483 | | | | | | 104 | | | | 115 | | | |
| CCG-102485 | | | | | | 102 | | | | 104 | | | |
| 575097 (CCG 102487) | | | | | | | | | | | | | |
| 575097 (trial 2) | | | | | | | 89 | 88 | 88 | 86 | 86 | | |
| CCG-102489 | | | | | | 106 | | | | 114 | | | |
| CCG-102491 | | | | | | 109 | | | | 112 | | | |
| 25203 | | | | 89 | | | 92 | 100 | 110 | 118 | 125 | 132 | 143 |
| CCG-102493 | | | | 93 | | 92 | 94 | 108 | 110 | 120 | 123 | 125 | 129 |
| CCG-102493 (trial 2) | | | | | | | 48 | | | | | | |
| CCG-102493 (trial 2) | | | | | | 102 | 100 | | | 95 | | | |
| CCG-102493 (trial 3) | 99 | 103 | | 104 | | 103 | | 107 | | 116 | | 131 | |
| CCG-102495 | | | | | | | 18 | | | | | | |
| AK968 | | | | | | | 96 | 105 | 112 | 117 | 124 | 123 | 130 |
| 1S-22207 | | | | | | 98 | 96 | 99 | | 113 | | | |
| 1S-22207 (trial 2) | | | | | | 96 | 101 | 111 | | 122 | | | |
| 1S-22207 (trial 3) | 96 | 98 | 100 | 101 | | | 98 | | | 106 | | | 126 |
| 1S-22207(trial 4) | 101 | 103 | 103 | 106 | | | 106 | | | 116 | | | 135 |
| 1S-22207 (trial 5) | 99 | 102 | 101 | 103 | | | 101 | | | 109 | | | 129 |
| 1S-22207 (trial 6) | 97 | 97 | 98 | 105 | | | 106 | | | 117 | | | 137 |
| 1S-26137 | | | | | | 89 | 89 | 91 | 105 | 98 | | | |
| 1S-30398 | | | | | | 98 | 98 | 99 | | 111 | | | |
| CCG-102620 | | | | | | 104 | 106 | 104 | | 115 | | | |
| CCG-102622 | | | | | | 99 | 100 | 103 | | 113 | | | |
| CCG-102624 | | | | | | 93 | 94 | 93 | | 87 | | | |
| CCG-102624 (trial 2) | 100 | 98 | 101 | 105 | | | 101 | | | 100 | | | 113 |
| CCG-203037 | 98 | 99 | 101 | 102 | | | 105 | | | 102 | | | 106 |
| CCG-203039 | 100 | 100 | 104 | 100 | | | 104 | | | 115 | | | 135 |
| CCG-203041 | 100 | 102 | 104 | 106 | | | 107 | | | 60 | | | 50 |
| CCG-203043 | 101 | 104 | 106 | 116 | | | 113 | | | 115 | | | 124 |
| CCG-203572 | | | | | | 97 | 97 | 96 | | 87 | | | |
| CCG-203572 (repeat) | 101 | 101 | 101 | 101 | | | 100 | | | 96 | | | 96 |
| CCG-203572 (trial 3) | 99 | 101 | 100 | 100 | | | 101 | | | 95 | | | 86 |
| CCG-203574 | | | | | | 102 | 95 | 85 | | 68 | | | |
| CCG-203576 | | | | | | 99 | 98 | 99 | | 101 | | | |
| CCG-203576 (trial 2) | 102 | 101 | 100 | 101 | | | 100 | | | 104 | | | 105 |
| CCG-203576 (trial 3) | 98 | 100 | 100 | 102 | | | 101 | | | 103 | | | 114 |

Example 15

In Vivo Efficacy

Figure 19:
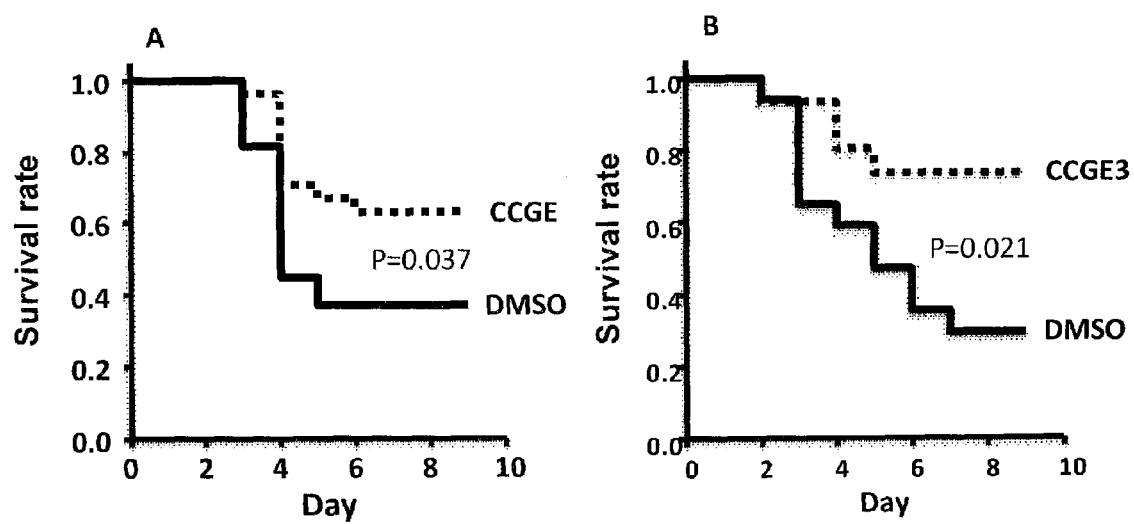
FIG. 19 shows A) Effects of small molecules 575096 (5 µg per day) on Tg+ mice survival after infection with $6*10^5$CFU UMAA2616. B) Effects of 1S-22207 (30 µg per day) on Tg+ mice survival after infection with $0.5-14*10^5$CFU UMAA2616.

This example describes the in vivo efficacy of compound 575096. Human plasminogen transgenic mice (Tg+) were first infected with $10^{5"6}$ CFUUMAA2616, then injected with 5-30 lag of test compound per mouse intraperitoneally daily for 5 days, starting one day after infection. Survival rates are shown in FIG. 19. A significant improvement in survival was observed for mice treated with 575096 compared to the DMSO control group (p=0.037) and also with analog 1S-22207 (p=0.021).

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A pharmaceutical composition that inhibits the pathogenticity of Group A *Streptococcus*, comprising a compound that inhibits the expression or activity of streptokinase from said Group A *Streptococcus*, wherein said compound is selected from the group consisting of

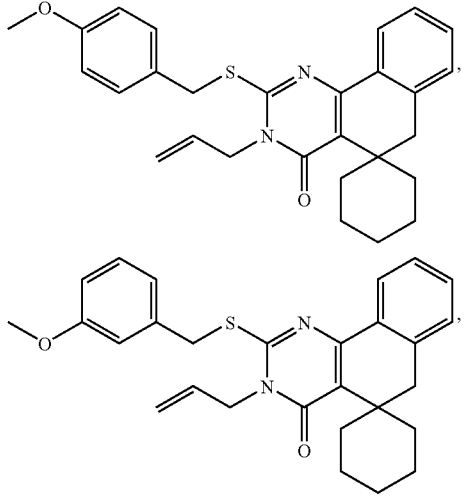

-continued

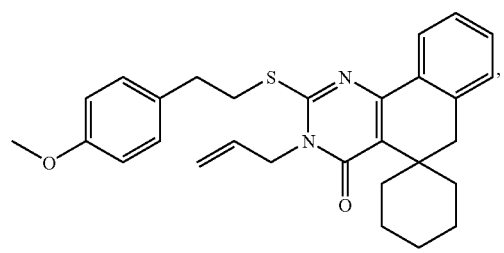

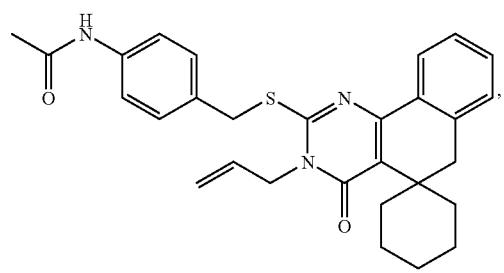

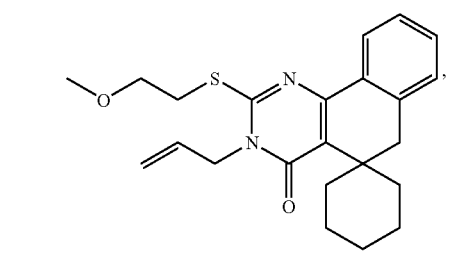

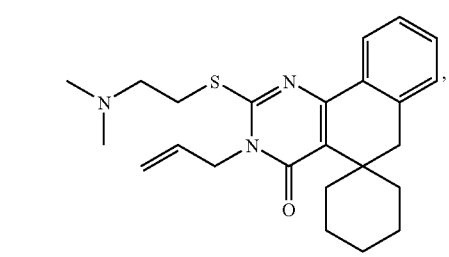

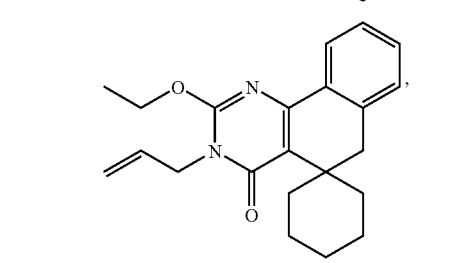

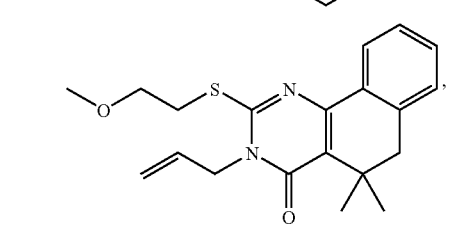

-continued

2. The composition of claim 1, further comprising a pharmaceutically acceptable carrier.

3. The composition of claim 1, wherein said composition inhibits infectivity of said Group A *Streptococcus*.

4. The composition of claim 1, wherein said composition further comprises a known antibiotic compound.

5. A method of inhibiting the pathogenticity of Group A *Streptococcus*, comprising contacting said Group A *Streptococcus* with a compound that inhibits the expression or activity of streptokinase from said Group A *Streptococcus*, wherein said compound is selected from the group consisting of

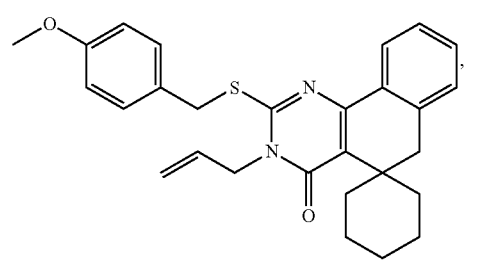
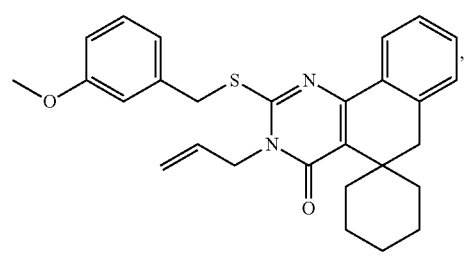
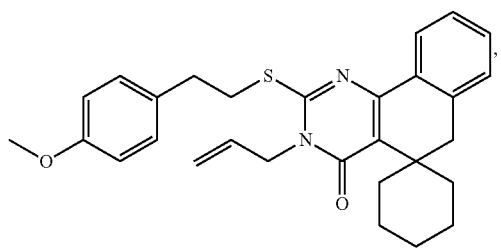
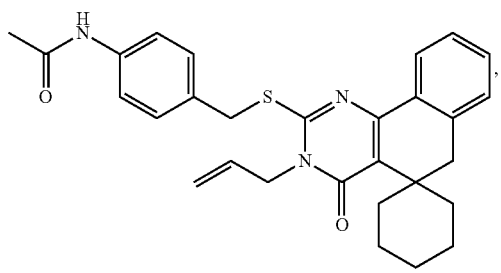
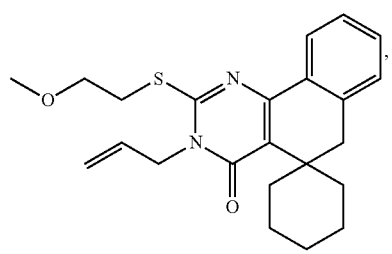
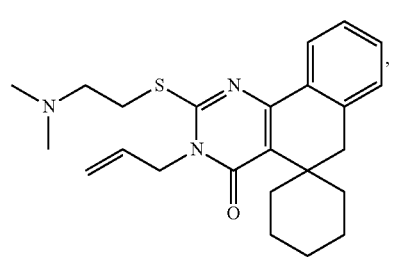
-continued
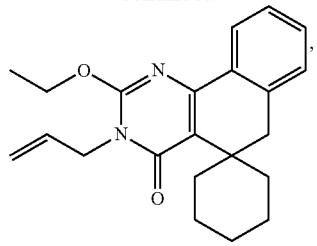
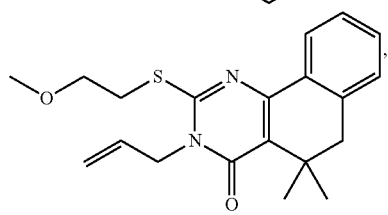
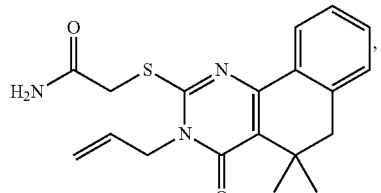
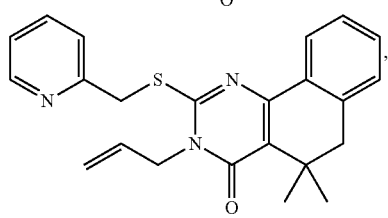
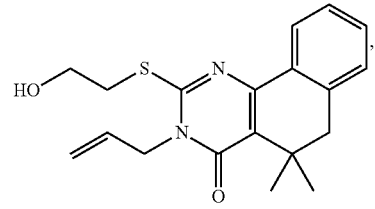
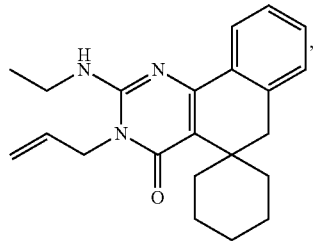
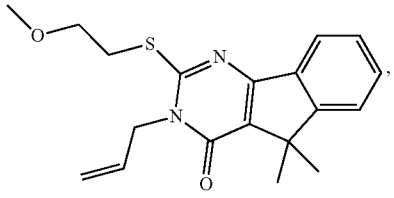
and -continued
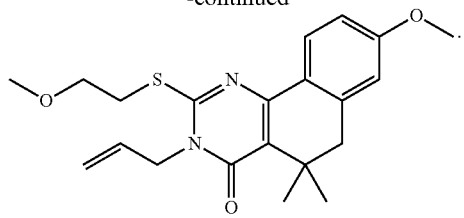
6. The method of claim 5, wherein said composition inhibits infectivity of said Group A *Streptococcus*.
7. The method of claim 5, further comprising the step of contacting said Group A *Streptococcus* with a known antibiotic compound.
* * * * *